US007820227B2

(12) United States Patent
Payne et al.

(10) Patent No.: US 7,820,227 B2
(45) Date of Patent: Oct. 26, 2010

(54) BIOLITHOGRAPHICAL DEPOSITION AND MATERIALS AND DEVICES FORMED THEREFROM

(75) Inventors: Gregory F. Payne, Cockeysville, MD (US); Gary W. Rubloff, Clarksville, MD (US); Hyunmin Yi, Lexington, MA (US); Rohan Fernandes, Beltsville, MD (US); Li-Qun Wu, North Potomac, MD (US); Reza Ghodssi, Silver Spring, MD (US); William E. Bentley, Annapolis, MD (US)

(73) Assignees: University of Maryland, College Park, College Park, MD (US); University of Maryland, Baltimore County, Baltimore, MD (US)

( * ) Notice: Subject to any disclaimer, the term of this patent is extended or adjusted under 35 U.S.C. 154(b) by 862 days.

(21) Appl. No.: 10/581,905

(22) PCT Filed: Feb. 20, 2004

(86) PCT No.: PCT/US2004/004853

§ 371 (c)(1),
(2), (4) Date: Apr. 16, 2007

(87) PCT Pub. No.: WO2005/061127

PCT Pub. Date: Jul. 7, 2005

(65) Prior Publication Data

US 2007/0275246 A1 Nov. 29, 2007

Related U.S. Application Data

(60) Provisional application No. 60/528,856, filed on Dec. 11, 2003.

(51) Int. Cl.
*A61L 33/00* (2006.01)

(52) U.S. Cl. .............. 427/2.1; 427/2.11; 427/2.12; 427/299; 427/300; 427/307; 427/322; 427/331; 427/372.2; 427/374.3; 427/384; 427/388.2; 427/388.4

(58) Field of Classification Search ................ 427/2.1, 427/2.11, 2.12
See application file for complete search history.

(56) References Cited

U.S. PATENT DOCUMENTS 4,103,064 A 7/1978 McAlear et al.

(Continued)

FOREIGN PATENT DOCUMENTS

JP 09-239396 A 9/1997

(Continued)

OTHER PUBLICATIONS

Hengsakul et al., Protein Patterning with a Photoactivatale Derivative of Biotin, Bioconjugate Chemistry 7, 1996, pp. 249-254.*

(Continued)

*Primary Examiner*—Michael Barr
*Assistant Examiner*—Andrew Bowman
(74) *Attorney, Agent, or Firm*—Jeffrey I. Auerbach; Edell, Shapiro & Finnan, LLC

(57) ABSTRACT

A method for biolithographical deposition of molecules is provided. According to an embodiment of the method, a reactive layer (e.g., a polysaccharide mass) having a surface region coated with a biologically compatible resist is provided. A portion of the biologically compatible resist is selectively removed to expose an exposed portion of the reactive layer. Molecules, such as biomolecules and/or cellular species, are then conjugated to the exposed portion of the reactive layer. Also provided are materials and devices related to the method.

23 Claims, 7 Drawing Sheets

U.S. PATENT DOCUMENTS

| | | |
|---|---|---|
| 7,014,749 B2 | 3/2006 | Redepenning |
| 2002/0084194 A1 | 7/2002 | Redepenning |
| 2006/0099456 A1 | 5/2006 | Redepenning |

FOREIGN PATENT DOCUMENTS

| | | |
|---|---|---|
| JP | 09-124703 | 11/1998 |
| WO | WO 00/11038 | 11/1999 |
| WO | WO 02/059395 A2 | 8/2002 |
| WO | WO 2004/018741 A1 | 3/2004 |

OTHER PUBLICATIONS

Yang et al., Photo-patternable gelatin as protection layers in low-tempearture surface micromachinings, Sensors and Actuators A 103, 2003, pp. 284-290.*

Beebe, David J. et al., Functional Hydrogel Structures For Autonomous Flow Control Inside Microfluidic Channels, Letters to Nature, vol. 404, Apr. 6, 2006.

Chen, Chia-Chun, Self-Assembly of Monolayers of Cadmium Selenide Nanocrystals with Dual Color Emission, Web Published Jul. 7, 1999, Langmuir 1999, 15, 6845-6850.

Chen, Guoping, et al., pH-Sensitive Thin Hydrogel Microfabricated by Photolithography, Published on the web Oct. 9, 1998, Langmuir 1998, 14, 6610-6612.

Chen, Tianhong, Enzymatic Methods for in Situ Cell Entrapment and Cell Release, Web Published Sep. 30, 2003, Biomacromolecules 2003, 4, 1558-1563.

Chen, Tianhong, Nature-Inspired Creation of Protein-Polysaccharide Conjugate and Its Subsequent Assembly onto a Patterned Surface, Web Published Oct. 3, 2003, Langmuir 2003, 19, 9382-9386.

Clark, Sarah L. et al. Engineering the Microfabrication of Layer-by-Layer Thin Films, Communications, Advanced Materials, Jul. 24, 1998.

Fernandes, Rohan Thermo-Biolithography: A Technique for Patterning Nucleic Acids and Proteins, Web Published Dec. 25, 2003, Langmuir 2004, 20, 906-913.

Fernandes, Rohan, Electrochemically Induced Deposition of a Polysaccharide Hydrogel onto a Patterned Surface, Web Published Apr. 15, 2003, Langmuir 2003, 19, 4058-4062.

Gao, Mingyuan, Lateral Patterning of CdTe Nanocrystal Films by the Electric Field Directed Layer-by-Layer Assembly Method, Web Published Mar. 27, 2002, Langmuir 2002, 18, 4098-4102.

Kastantin, Mark J., Integrated Fabrication of Polymeric Devices for Biological Applications, Journal of Sensors and Materials, Special Issue on Biomedical Applications, Inc. Press, Published September 2003.

Muzzarelli, Riccardo A. A. et al., Tyrosinase-mediated quinine tanning of chitinous materials, Carbohydrate Polymers 211 (1994) 295-300.

O'Connor, Stephen M. et al., Immobilization of neural cells in three-dimensional matrices for biosensor applications, Biosensors & Bioelectronics 14 (2000) 871-881.

O'Connor, Stephen M. et al., Immobilization of neural cells in three-dimensional matrices for biosensor applications, Biosensors & Bioelectronies 14 (2000) 871-881.

Payne, Gregory F. et al., Tyrosinase Reaction/Chitosan Adsorption for Selectively Removing Phenols from Aqueous Mixtures, Biotechnology and Bioengineering, vol. 40 p. 1011-1018 (1992).

Seong, Gi Hun et al., Fabrication of Microchambers Defined by Photopolymerized Hydrogels and Weirs within Microfluidic Systems: Application to DNA Hybridization, Anal. Chem. 2002, 74, 3372-3377.

Sirkar Kaushik et al. , Amperometric Biosensors Based on Oxidoreductases Immobilized in Photopolymerized Poly(ethylene glycol) Redox Polymer Hydrogels, Anal. Chem. 1998, 2888-2894.

Sun, Wei-Qiang et al., Tyrosinase-Containing Chitosan Gels: A Combined Catalyst and Sorbent for Selective Phenol Removal, Biotechnology and Bioengineering, vol. 51, pp. 79-86 (1996) John Wiley & Sons Inc.

Takenaka, Shinsuke et al., Sol-gel preparation of single-layer, 0.75 um thick lead zirconate titanate films from lead nitrate-titanium and ziroconium alkoxide solutions containing polyvinylpyrrolidone, Applied Physics Letters, vol. 79, No. 21, pp. 3845-3847, Published Nov. 19, 2001.

Tatsumi, Kenji, Removal of Penols From Wastewater by an Enzyme and Chitosan, Advances in Chitin Sciences 1997, vol. 2, pp. 864-869.

Wada, Shinji, Removal of Phenols and Aromatic Amines from Wastewater by a Combination Treatment with Tyrosinase and a Coagulant, Biotechnology & Bioengineering, vol. 45, pp. 304-309, (1995).

Wu, Li-Qun, Chitosan-Mediated and Spatially Selective Electrodeposition of Nanoscale Particles, Web Published Mar. 17, 2005, Langmuir 2005, 21, 3641-3646.

Wu, Li-Qun, Spatially Selective Deposition of a Reactive Polysaccharide Layer onto a Patterned Template, Web Published Jan. 4, 2003, Langmuir 2003, 19, 519-524.

Wu, Li-Qun, Voltage-Dependent Assembly of the Polysaccharide Chitosan onto an Electrode Surface, Web Published Sep. 21, 2003, Langmuir 2002, 18, 8620-8625.

Yi, Hyunmin, A Robust Technique for Assembly of Nucleic Acid Hybridization Chips Based on Electrochemically Templated Chitosan, Web Published Dec. 6, 2003, Article published in Jan. 15, 2004 in Analytical Chemistry, vol. 76, No. 2.

Zhitomirsky, Petric A. et al., Cathodic electrodeposition of polymer films and organoceramic films, Materials Science and Engineering B78 (2000) 125-130, Published by Elsevier Sciences S.A. 2000.

* cited by examiner

Soluble ⇌ Insoluble + xH⁺

⊢—⊣
1mm

Fig. 9A
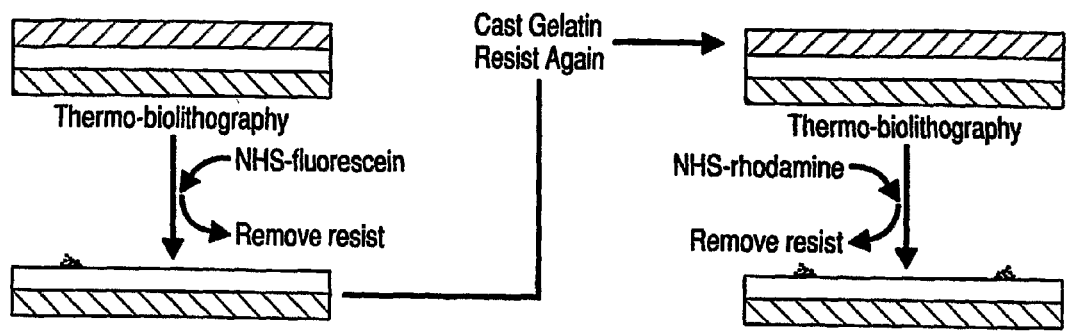
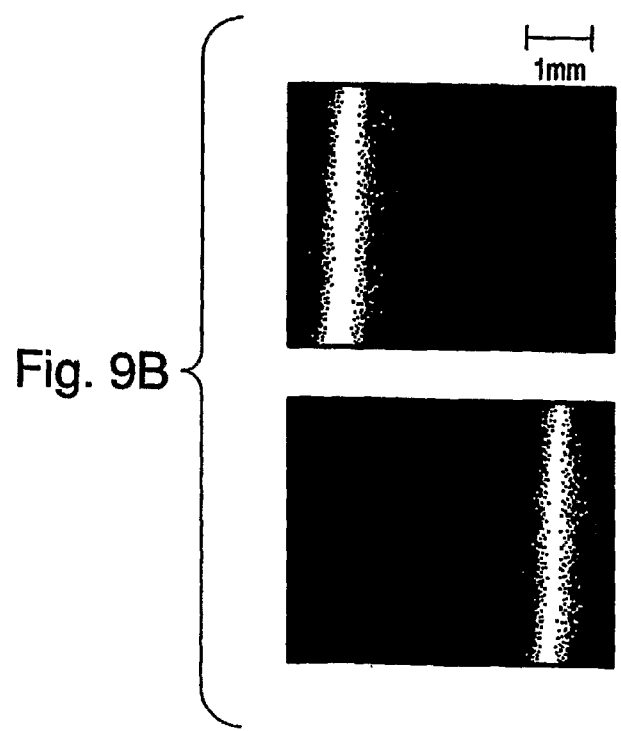
Fig. 9B

First Patterning Step
Patterning of GFP

Second Patterning Step
Patterning of rhodamine

Fluorescence Intensity

Distance From Left End (mm)

Fluorescence Intensity

BIOLITHOGRAPHICAL DEPOSITION AND MATERIALS AND DEVICES FORMED THEREFROM

RELATED APPLICATIONS

This application claims the benefit of priority of U.S. provisional application No. 60/528,856 filed in the U.S. Patent & Trademark Office on Dec. 11, 2003 entitled "Thermo-BioLithography: A Technique for Patterning Nucleic Acids and Proteins," the complete disclosure of which is incorporated herein by reference.

GOVERNMENT LICENSING CLAUSE

The U.S. Government has a paid-up license in this invention and the right in limited circumstances to require the patent owner to license others on reasonable terms as provided for by the terms of Grant No. 2001-35504-10667 awarded by the United States Department of Agriculture.

BACKGROUND OF THE INVENTION

1. Field of the Invention

This invention relates generally to methods for controlled and selective deposition of one or more species of molecules, especially but not necessarily biomolecules, cellular species, and the like, onto a reactive layer. This invention further relates to materials and to devices comprising the deposited molecules.

2. Description of Related Art

The use of micro-electro-mechanical systems (MEMS) in biological research is becoming increasingly common. Micro-devices allow for relatively easy observation and manipulation of individual cells, proteins, or other biological macromolecules. Sample sizes for such experiments may be reduced when using MEMS as compared to traditional techniques. J. D. Trumbull, et al., *IEEE Transactions on Biomed. Eng.* 47, 3 (2000). This allows biological systems to be studied at a new level of resolution while minimizing the materials required for an experiment.

Initially, microfluidic devices were used primarily for capillary electrophoresis. S. Jacobson, et al., *Anal. Chem* 66 (1994) 1114; D. J. Harrison, et al., *Anal. Chem.* 64 (1992) 1926; Z. Liang, et al.; *Anal. Chem.* 68 (1996) 1040. Recently, there has been interest in incorporating a complete array of functional units, e.g., valves, pumps, reaction chambers, etc., onto a single chip to create a lab-on-a-chip (LOC). J. Voldman, et al., *J. Microelectromech. Sys.* 9 (2000) 295; I. Glasgow, et al., *IEEE Transactions on Biomed. Eng.* 48 (2001) 570; T. Fujii, *Microelectronic Eng.*, 61-62 (2002) 907; A. Yamaguchi, et al., *Analytical Chimica Acta.*, 468 (2002) 143; J. H. Kim, et al., *Sensors and Actuators A.* 95 (2002) 108; M. Krishnan, et al., *Curr. Opinion Biotech.* 12 (2001) 92; A. Hatch, et al., *J. Microelectromech. Sys.* 10 (2002) 215.

The ability to create MEMS and other devices such as biosensors and microarrays requires facile methods to precisely control surfaces. A variety of patterning techniques can be used to produce desired structures, while various methods have been investigated to control surface chemistries. For instance, microfabrication techniques are routinely applied to create patterned inorganic surfaces with nanometer to micrometer scale resolution. Xia, Y., et al., *Angew. Chem, Int. Ed. Engl.*, 37, 550-575 (1998).

Two approaches have emerged to extend microfabrication techniques for the creation of patterned surfaces with organic and biological materials. The first approach is based on an extension of photolithography. Bain, C. D., et al., *Angew. Chem., Int. Ed. Engl.*, 28, 506-512 (1989); Whitesides, G. M., Langmuir, 6, 87-96 (1990). Self-assembled monolayers are selectively irradiated to create a pattern of freshly exposed surface, which is then reacted with a bifunctional agent. Reactions include those between thiols and metal surfaces, or between silanes and oxidized silicon. Bain, C. D., et al., *Chem. Int. Ed. Engl.* 28, 506-512 (1989); Whitesides, G. M., et al., *Langm.*, 6, 87-96 (1990); Sagiv, J. *J. Am. Chem. Soc.* 102, 92-98 (1980); Brzoska, J. B., et al., *Langm.*, 10, 4367-4373 (1994); Allara, D. L., et al., *Langm.*, 11, 2357-2360 (1995).

A first functional group of the agent attaches the agent to the freshly exposed surface, and the second functional group subsequently couples the molecules of interest. Although variations exist, lithography creates the spatial template upon which subsequent coupling occurs. Vossmeyer, T., et al., *Angew. Chem., Int. Ed. Engl.*, 36, 1080-1083 (1997); Vossmeyer, T., et al., *J. Appl., Phys.*, 84, 3664-3670 (1998); Jones, V. W., et al., *Anal. Chem.*, 70, 1233-1241 (1998); Harnett, C. K., Langmuir, 17, 178-182 (2001); Jonas, U., et al., *Proc. Natl. Acad. Sci. USA.*, 99, 5034-5039 (2002). This first approach has a drawback associated with the need for photo-sensitive reagents that can be expensive, hazardous and require cumbersome steps to prepare the surface. Furthermore, conventional photolithographic operations require "line-of-sight" and would be difficult to accomplish on internal surfaces in an enclosed microfluidic system. Alternatively, if the lithographic patterning and subsequent biological functionalization are carried out before the microfluidic device is covered to form a closed fluidic environment, the biofunctionality internal to the microfluidic system cannot be readily reprogrammed. Finally, since many biospecies are labile, i.e., sensitive and delicate with respect to their environmental conditions, fabrication processes required to close the microfluidic system may degrade the biospecies.

The second approach for creating patterned surfaces with organic and biological materials is microcontact printing (μCP), in which a soft stamp (typically made of poly-dimethylsiloxane) is created with a preselected pattern. After "inking" the stamp with a solution containing the material to be deposited, the stamp is pressed onto a surface to transfer the pattern. Xia, Y., et al., *Langmuir,* 12, 4033-4038 (1996); Hidber, P. C. et al., *Langmuir,* 12, 1375-1380 (1996). Microcontact printing entails many of the same drawbacks as the lithography discussed above. Other drawbacks to the microcontact printing approach involve difficulties in stamping with high spatial resolution. Furthermore, the need for direct contact to the surface entails the drawbacks described above for applications to enclosed microfluidic systems. Vaeth, K. M., et al., *Langmuir* 2000, 16, 8495-8500.

Another approach to patterning biomolecules on surfaces is "dip-pen" nanolithography, in which scanning probe microscopy (like atomic force microscopy) is used to write species onto a surface with high lateral resolution. For biomolecular species this is accomplished by transport from the writing tip through a water meniscus to the substrate. While the lateral spatial resolution of this patterning method can be very high (30 nm), patterns are written in serial fashion, entailing the throughput limitations associated with other direct-write approaches such as electron and ion beam lithographies. In addition, dip-pen nanolithography entails the drawbacks described above for applications to enclosed microfluidic systems. Piner, R. D., et al., *Science* 283, 661-663 (1999); Jong, S., Mirkin, C. A., *Science,* 288, 1808-1811 (2000); Lyuksyutov, S. F. et al., *Nature Materials,* 2, 468-474 (July 2003).

Electrophoretic deposition has also been used to assemble colloidal particles and proteins onto electrode surfaces. This approach has been extended to exploit an electric field to direct the spatially selective deposition of CdTe nanocrystals. Gao, M, et al., *Langmuir*, 18, 4098-4102 (2002). In this method, a surface with patterned electrodes is first fabricated, then a combination of an applied voltage and layer-by-layer assembly is used to generate multilayers with spatial resolution in lateral directions. A drawback to this assembly approach is that voltages are maintained to retain the initial layer of nanocrystals, which may not be held to the surface by strong chemical bonds or insolubility. Again, it is not clear whether these layer-by-layer approaches can be extended to enclosed microfluidic channels.

Another drawback to several of the above approaches is that the deposited film provides a non-aqueous or hydrophobic microenvironment that is less appropriate than aqueous or hydrophobic environments for some sensitive biological systems. Ito, Y., et al., *Langmuir*, 13, 2756-2759 (1997). For example, in the case of proteins, a non-aqueous microenvironment or hydrophobic surface may be denaturing, as proteins tend to unfold, when immobilized, which often causes loss of activity and binding sites that may be dependent upon the three-dimension structure.

SUMMARY OF THE INVENTION

It is an object of the present invention to provide a method for controlling the deposition and conjugation of molecules, especially biomolecules and/or cellular species, onto an organic reactive layer, such as a polysaccharide mass, preferably yet optionally in a spatially selective manner.

It is another object of the present invention to provide a method for controlling the deposition and conjugation of a plurality of molecular species, such as biomolecular and/or cellular species, onto an organic reactive layer, such as a polysaccharide mass, preferably yet optionally in a spatially selective manner.

Another object of the present invention is to provide a material comprising one or more molecular species, such as biomolecular and/or cellular species, deposited on and conjugated to an organic reactive layer, such as a polysaccharide mass.

Still another object of the invention is to provide patterned biomicrofluidic systems comprising materials of the present invention and/or prepared from methods of the present invention.

To achieve one or more of the foregoing objects, and in accordance with the purposes of the invention as embodied and broadly described in this document, an aspect of this invention provides a method for selective deposition of molecules. The method comprises providing a reactive layer (e.g., a polysaccharide mass) comprising a surface region coated with a biologically compatible resist, selectively removing a portion of the biologically compatible resist to expose a portion (hereinafter sometimes referred to as "an exposed portion") of the reactive layer, and conjugating molecules with the exposed portion of the reactive layer.

Also to achieve one or more of the foregoing objects, and in accordance with the purposes of the invention as embodied and broadly described in this document, another aspect of this invention provides a method for the selective deposition of a plurality of molecular species. The method comprises providing a reactive layer (e.g., polysaccharide mass) comprising a surface region coated with a biologically compatible resist, selectively removing a first portion of the biologically compatible resist to expose a first exposed portion of the reactive layer, conjugating a first molecular species to the first exposed portion of the reactive layer, covering the first exposed portion, selectively removing a second portion of the biologically compatible resist to expose a second exposed portion of the reactive layer, and conjugating a second molecular species to the second exposed portion of the reactive layer.

Additional aspects of the invention are directed or relate to materials and devices comprising a reactive layer having a surface with a spatially selected portion thereof conjugated to one or more molecular species.

BRIEF DESCRIPTION OF THE DRAWINGS

The accompanying drawings are incorporated in and constitute a part of the specification. The drawings, together with the general description given above and the detailed description of the certain preferred embodiments and methods given below, serve to explain the principles of the invention.

FIG. 6A shows a thermo-biolithographic approach for patterning nucleic acids according to an embodiment of the invention, as carried out in Example 2.

FIG. 9A illustrates a first approach for an embodiment comprising sequential thermo-biolithography, as carried out in Example 4.

FIG. 9B shows fluorescence photomicrographs for the sequential thermo-biolithography carried out in the first approach of FIG. 9A. The upper fluorescence photomicrograph was taken using an excitation filter of 480 nm (bandwidth 40 nm), an emission barrier filter of 510 nm, and an exposure time of 50 seconds. The lower fluorescence photomicrograph was taken using an excitation filter of 560 nm (bandwidth 40 nm), an emission barrier filter of 610 nm, and an exposure time of 50 seconds.

DETAILED DESCRIPTION OF PREFERRED EMBODIMENTS AND PREFERRED METHODS

Reference will now be made in detail to the presently preferred embodiments and methods of the invention as illustrated in the accompanying drawings. It should be noted, however, that the invention in its broader aspects is not limited to the specific details, representative assemblies and methods, and illustrative examples shown and described in this section in connection with the preferred embodiments and methods. The invention according to its various aspects is particularly pointed out and distinctly claimed in the attached claims read in view of this specification, and appropriate equivalents.

It is to be noted that, as used in the specification and the appended claims, the singular forms "a," "an," and "the" include plural referents unless the context clearly dictates otherwise.

As used herein and unless otherwise indicated, a "hydrogel" is defined as a semi-solid, multi-component (i.e., two or more component) system comprising a three-dimensional network of one or more species of polymer chains, and water filling or substantially filling the space between macromolecules. Without wishing to be bound by any theory, it is believed that the water is bound in the network by an osmotic effect. Depending on the properties of the polymer (or polymers) used, as well as on the nature and density of the network, such structures in equilibrium can contain various amounts of water. Typically in the swollen state the mass fraction of water in a hydrogel is equal to or higher than the mass fraction of polymer, and often is as high as 80 weight percent, and in some cases as high as 95 weight percent or even 99 weight percent (w/w). Two general classes of hydrogels can be defined:

Physical gels (pseudogels), in which the polymer chains are connected by electrostatic forces, hydrogen bonds, hydrophobic interactions or chain entanglements; such gels are non-permanent and sometimes can be converted to polymer solutions by altering conditions (e.g., heating); and Chemical hydrogels (true or permanent gels) in which covalent bonds link the polymer chains together.

As used herein, a "solid compact film" is defined as a polymer (e.g., polysaccharide) deposit that is free or substantially free of entrapped water.

Figure 1:
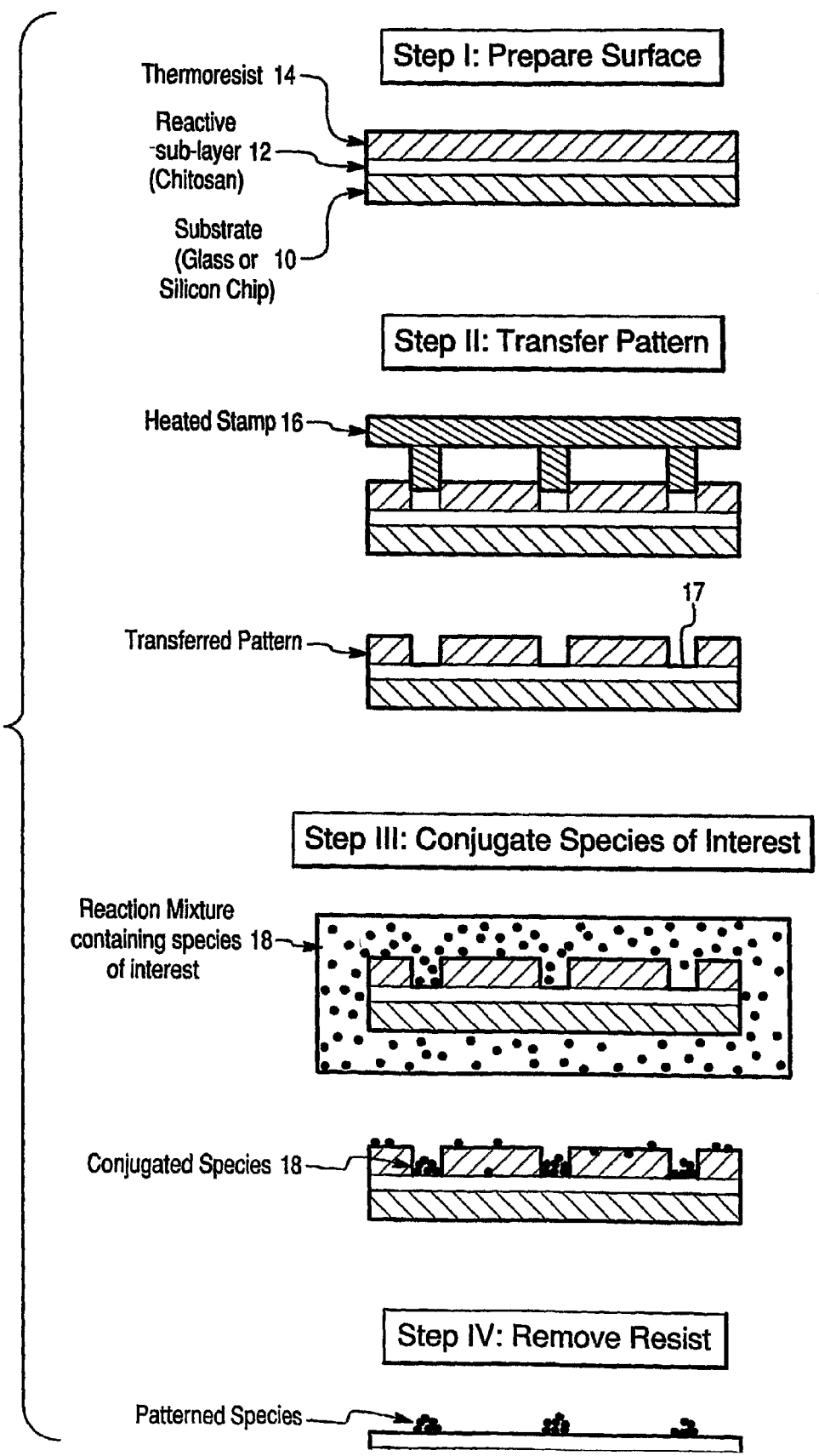
FIG. 1 shows a thermo-biolithographic approach for depositing and conjugating a molecular species on a reactive layer.

According to a first embodiment of the present invention generally illustrated in FIG. 1, a method is provided for biolithographical deposition of molecules, comprising:

(a)(i) providing a substrate or support 10;

(a)(ii) depositing on the substrate a reactive layer 12 (e.g., a polysaccharide mass);

(a)(iii) coating a surface region of the reactive layer with a biologically compatible resist 14;

(b) selectively removing a portion of the biologically compatible resist, for example with a heat stamp 16, to uncover an exposed portion 17 of the reactive layer;

(c) conjugating one or more molecular species 18 with the exposed portion of the reactive layer; and (d) optionally removing the biologically compatible resist from the reactive layer while maintaining the conjugated molecules on the reactive layer to provide a pattern of conjugated molecules.

Selective deposition and conjugation of the molecules at the exposed portions of the underlying reactive layer, but not at unexposed portions, creates a pattern of conjugated molecules.

According to a second embodiment of the invention, the selective exposure and bonding process steps may be repeated once, twice, thrice, or a higher plurality of iterations to deposit and conjugate a plurality of molecular species to a common reactive layer, the molecular species being the same or different from one another. According to this embodiment, the method comprises:

(a)(i) providing a substrate;

(a)(ii) depositing on the substrate a reactive layer (e.g., a polysaccharide mass);

(a)(iii) coating a surface region of the reactive layer with a biologically compatible resist;

(b) selectively removing a first portion of the biologically compatible resist, for example with a heat stamp, to expose a first exposed portion of the reactive layer;

(c) conjugating a first molecular species with the first exposed portion of the reactive layer;

(d) coating the first molecular species conjugated to the first exposed portion of the reactive layer with the biologically compatible resist;

(e) selectively removing a second portion of the biologically compatible resist to expose a second exposed portion of the reactive layer;

(f) conjugating a second molecular species with the second exposed portion of the reactive layer; and (g) optionally removing the biologically compatible resist from the reactive layer while maintaining the conjugated first and second molecular species on the reactive layer.

The second exposed portion preferably yet optionally is spatially separate from the first exposed portion. Also preferable yet optional, the first and second molecular species are conjugated with the reactive layer sequentially. Preferably yet optionally the first molecular species differs from the second molecular species.

It is to be understood that the herein discussed and other embodiments falling within the scope of this invention may comprise fewer or more steps than those described and illustrated. For example, in the above-described second embodiment, steps (c) and (d) may be interceded with a step of removing the entire biologically compatible resist, in which case step (d) optionally comprises recoating the surface region of the reactive layer, including the conjugated first molecular species, with the biologically compatible resist.

(a)(i) Substrate and Support

A substrate comprises a platform, wafer, or support on which the reactive layer may be formed, transferred to, or otherwise provided. The substrate may comprise one or more materials, may be homogeneous or heterogeneous, and may contain a surface film. The substrate surface may be flat, curved, multi-leveled, etc., and may optionally include channels (e.g., microchannels), ridges, indentations, protuberances, and the like. The substrate and substrate surface are preferably substantially electrically non-conducting. Substrates may be made of inorganic materials such as, but not necessarily limited to, a silicon wafer optionally having a surface oxide film. Other inorganic materials include silicon oxide, silicon nitride, the like, and others.

The substrate includes one or more surface portions on which an electrically conductive support is optionally provided. The provision of an electrically conductive support is optional, although especially useful in the event that the reactive layer (e.g., polysaccharide mass) is to be deposited electrochemically, as described in further detail below. As referred to herein, the surface portion on which the support is optionally provided may mean less than the entire substrate surface, and may also encompass an entire substrate surface. In the event that the electrically conductive support is provided on some but not the entire substrate surface, the portion of the substrate surface without the electrically conductive support is preferably an electrically non-conductive portion. The electrically conductive support may constitute part of the substrate, may be formed integrally with the substrate, or may be formed on or attached to the substrate surface. The electrically conductive support may include a support surface that is coplanar or not coplanar (offset) with respect to the electrically non-conductive portion of the substrate surface, e.g., as in the case of microchannels.

In embodiments of the invention, especially embodiments involving the electrochemical deposition of the reactive layer (e.g., polysaccharide mass), the electrically conductive support and electrically non-conductive portion may optionally define a pattern. As referred to herein, a pattern refers to the spatial localization of a material, i.e., so that the substrate surface contains an electrically conductive portion and an electrically non-conductive portion. The pattern may extend from one surface of the substrate to another substrate surface, or may be localized on a single surface or a portion of a single surface. A pattern may comprise a repeating arrangement of objects or shapes, a non-repeating or random arrangement of objects or shapes, a particular defined shape, array, or the like. For example, the pattern may comprise a plurality of parallel lines spaced apart from one another by uniform or non-uniform intervals.

The material or materials selected for the electrically conductive support may be those upon which the reactive layer (e.g., polysaccharide mass) may be deposited via electrochemical deposition. Suitable materials include but are not necessarily limited to metals (e.g., aluminum, antimony, cadmium, chromium, cobalt, copper, gold, iron, lead, magnesium, mercury, nickel, palladium, platinum, silver, steel, tin, tungsten, zinc), metal alloys, semiconductors, and conductive polymers (e.g., polypyrrole, etc.).

Figure 2:
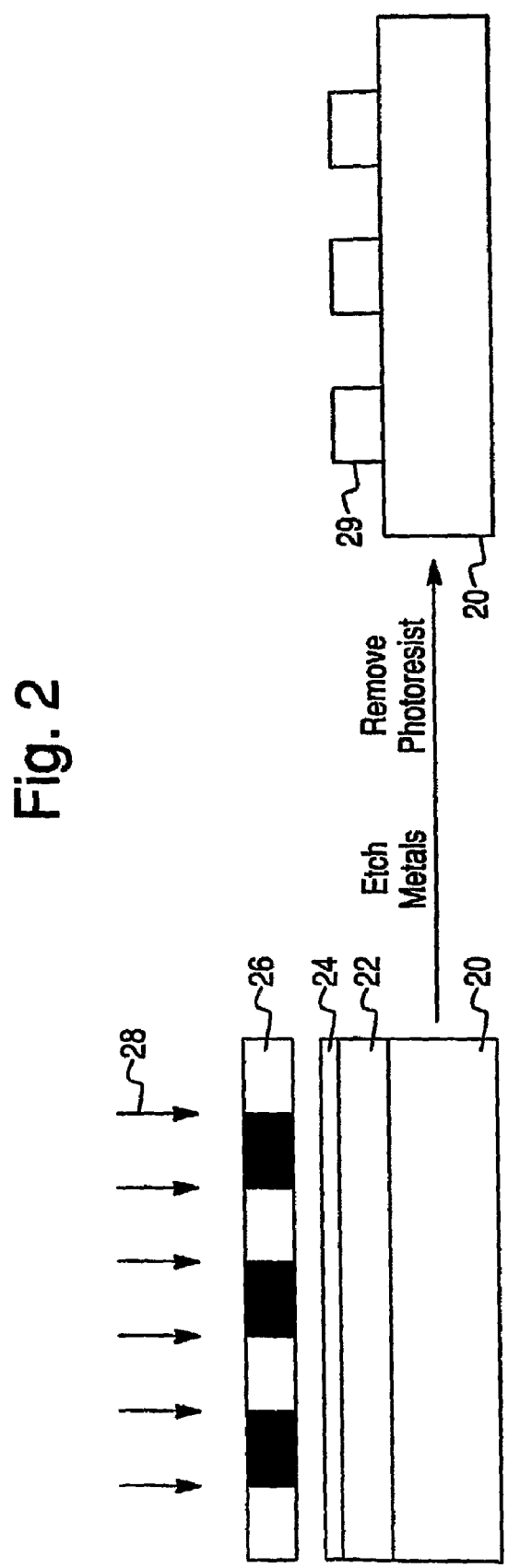
FIG. 2 shows a progression of steps of a microfabrication technique for establishing an electrically conductive (e.g., metal) pattern on a substrate.

Deposition of the electrically conductive support on the substrate may be accomplished by any known or suitable technique. For example, standard microfabrication techniques may be selected to pattern or otherwise apply an electrically conductive material, e.g., gold, onto an electrically insulative substrate. Referring to FIG. 2, there is shown an exemplary yet not necessarily limiting technique for patterning an electrically conductive material on a substrate. In FIG. 2, the selected substrate 20 comprises silicon wafers with a thermal oxide film. A metal layer or layers 22, for example chromium and gold in the illustrated embodiment, are sputtered (simultaneously or consecutively) or otherwise deposited onto the wafer 20 to provide a bi-layer metal structure. Next, the deposited metal is optionally covered with a primer, then a photoresist 24 is applied to the primed metal surface, e.g., via conventional spin-coating techniques. A mask 26 is placed over the photoresist, and the photoresist is then patterned, for example, by exposure of the unmasked portions of the photoresist to UV light 28. The exposed, non-masked areas are then etched with a suitable etchant to develop the sputtered metals into a pattern. The photoresist then is removed, such as with a solvent, e.g., acetone, leaving the patterned sputtered metal support(s) 29 over the substrate 20.

(a)(ii) Deposition of Reactive Layer

Deposition of the reactive layer may be performed in accordance with any suitable technique. An example of such a technique is electrochemical deposition, in which the patterned electrically conductive support serves as a platform for the electric field directed deposition of reactive layer. Another deposition technique comprises casting, for example, by dissolving a polymer in a solvent, spreading the polymeric solution onto the platform surface, and evaporating the solvent to form a polymeric reactive layer.

It is to be understood that in certain embodiments of the invention, including those elaborated upon below, the phrase "deposit on" or "depositing on" may comprise depositing the reactive layer indirectly on the patterned electrically conductive support (or substrate), such as in the case of depositing the reactive layer onto a predeposited film (e.g., chitosan film) that has already been deposited on the support.

The reactive layer may be deposited on the entire surface (or surfaces) of the substrate, or on less than the entire surface. According to an embodiment of the invention, the reactive layer is deposited on the electrically conductive support of the substrate surface, but not the optional electrically non-conductive portion. Thus, the deposition of the reactive layer is spatially selective based on the pattern of the electrically conductive support, especially in the case of a deposited solid compact film. It should be understood, however, that due to the semi-solid physical structure of a hydrogel, deposition of a hydrogel on a conductive support may sometimes spread slightly over the conductive/non-conductive interface, onto the peripheral region of the non-conductive portion.

The reactive layer preferably comprises an organic polymer and/or organic oligomer, especially those capable of controlled solubilization and insolubilization, such as via pH adjustment. For the purpose of describing the invention hereinafter, but not necessarily by limitation, the reactive layer will be exemplified as polysaccharide mass comprising or formed from an insolubilizable polysaccharide capable of solubilizing in a liquid medium, preferably aqueous, and forming or otherwise depositing a layer or layers on an electrically conductive support (or predeposited layers on a support). Other examples of reactive layers include proteins, such as polylysine.

(a)(ii)(A) Polysaccharides and Other Reactive Layers

The reactive layer of embodiments of the present invention preferably comprises or is derived from a composition comprising selectively insolubilizable polysaccharides capable of solubilizing in a liquid medium, preferably aqueous, and forming or otherwise depositing an insoluble polysaccharide layer or layers onto a support (or predeposited layers on a support) under effective reaction conditions. As used herein, the term polysaccharide includes starches and polysugars, particularly polymers containing glucosamine residues. Ionizable polysaccharides include carboxymethylcellulose, chitosan, chitosan sulfate, pectin, alginate, glycosaminoglycans, ionizable agar, and carrageen. Other synthetic polymers include, for example, polymethacrylic acid, ligninsulfonates, polyvinylsulfonic acid, polyvinylphosphonic acid and polyethyleneimine; similar extracts of plants also may be used. Other suitable polysaccharides include gums from trees, pectins from fruits, starches from vegetables, and celluloses from woody fibers. Chitosan is the preferred ionizable polysaccharide of the present invention.

In preferred embodiments, the selective insolubilization and solubilization of the polysaccharides of the present invention is accomplished by modifying one or more of the polysaccharide ionizable group(s), which may be the same or different. At one or more range(s) of pH the polysaccharide will be soluble in an aqueous solvent ("solubilizing pH ranges"), whereas at one or more other pH values range(s), the polysaccharide will be insoluble (or less soluble), and thus be capable of forming an insoluble mass (e.g., hydrogel and/or compact film) deposited on a support. Suitable ionizable groups include those ionizable at low pH, e.g., capable of forming a positive charge (e.g., alkyl amine groups, primary, secondary or tertiary amine groups, guanidinium groups, imidazole groups, indole groups, purine groups, pyrimidine groups, pyrrole groups, etc.) and those that are ionizable at high pH, e.g., capable of forming a negative charge (e.g., alkoxide groups, carboxyl groups, hydroxy acid groups, phenolic groups, phosphate groups, sulfhydryl groups, etc.). Suitable groups may exhibit multiple pKs, which may be the same (e.g., polyacidic or polybasic) or different (e.g., zwitterionic). For selectively insolubilizable polysaccharides that are ionizable at low pH, amine groups are preferred; for selectively insolubilizable polysaccharides that are ionizable at high pH, carboxyl groups are preferred.

(a)(ii)(B) Chitosan

A preferred selectively insolubilizable polysaccharide is pH-responsive, nucleophilic chitosan, which is an amine-rich polysaccharide derived by deacetylation of chitin. Chitin is the second most abundant polysaccharide in nature and is found in crustaceans, insects, and fungi. Chitosan is also commercially available, such as from various suppliers (e.g., Aldrich, Sigma). The term chitosan includes chitosan polymers and oligomers with complete or substantially complete deacetylation, or chitosan with less than complete deacetylation. Chitosan also includes various derivatives of chitosan having the necessary solubility for this invention and at least a portion of the amino functional groups available for reaction.

Figure 3:
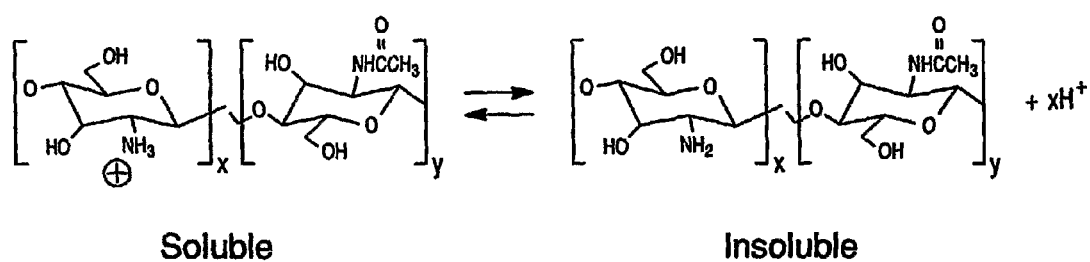
FIG. 3 shows the transformation of a selectively insolubilizable polysaccharide chitosan from a soluble phase to an insoluble phase.

Chitosan has primary amino groups that have pKa values of about 6.3. At pHs below the pKa, amino groups are protonated making chitosan a water-soluble, cationic polyelectrolyte. At pHs above the pKa of about 6.3, chitosan's amino groups are deprotonated, and the chitosan polymer becomes insoluble. The transformation of the selectively insolubilizable polysaccharide chitosan from a soluble phase to an insoluble phase is shown in FIG. 3. The pH-dependent solubility of chitosan allows the biopolymer to be processed in an aqueous solution, and brought out of solution and formed into various shapes (e.g., beads, membranes, and films) by imparting a modest increase in pH, e.g., to neutrality.

(a)(ii)(C) Deposition

Exemplary methods for depositing the reactive layer onto a selected surface or surface portion of the substrate will now be described further.

According to one preferred method, the reactive layer is prepared from a pH-responsive, selectively insolubilizable polymer or oligomer, and more preferably a selectively insolubilizable polysaccharide. Conversion of the selectively insolubilizable polysaccharide between a soluble state and an insoluble state is controlled by adjustment to the pH of the solution containing the polysaccharide. In this embodiment, the polysaccharide is introduced onto the support in a solubilized state, then its pH is adjusted to insolubilize the polysaccharide and form a deposited mass.

Another embodied method for depositing a polysaccharide deposit on an electrically conductive support according to an embodiment of the present invention will now be described with reference to FIG. 4. It is to be understood that the materials and compositions of this invention are not necessarily produced by the described embodiments and equipment, i.e., other methods and equipment may be used.

Figure 4:
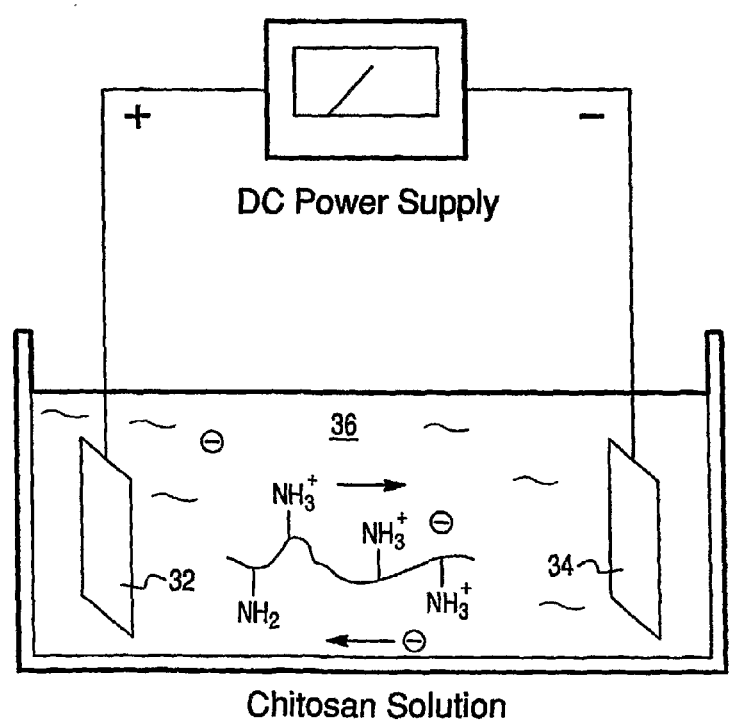
FIG. 4 shows a simplified representation of an electrochemical deposition cell for carrying out certain embodied methods of the invention.

FIG. 4 shows a suitable electrochemical deposition assembly for depositing the polysaccharide mass onto a non-patterned or patterned substrate. The assembly comprises a power source 30, such as a DC source, and a positive electrode 32 (anode) and a negative electrode 34 (cathode) connected to the power source with appropriate wiring or electrical connections. The electrodes 32 and 34 are immersed in an aqueous solution 36 comprising the selectively insolubilizable polysaccharide, preferably in a solubilized state. Electrodeposition of the polysaccharide is accomplished by application of an electrical voltage between the electrodes 32 and 34.

Chemical deposition of the selectively insolubilizable polysaccharide is preferably electrode selective, providing another degree of control over the process. Polysaccharides containing a group ionizable at a low pH, e.g., capable of forming a positive charge, are attracted to and deposit on the negative electrode. Accordingly, for such polysaccharides the electrically conductive support is polarized to serve as the negative electrode. The shape of the electrically conductive support on which the polysaccharide deposits largely dictates the spatial distribution and localization of the deposited polysaccharide. Positively charged polysaccharides are neither attracted to nor deposit on the positive electrode. The positive (or counter) electrode may be, for example, a non-patterned metal-coated (e.g., gold-coated) silicon wafer. Examples of groups ionizable at a low pH include alkyl amine groups, primary, secondary or tertiary amine groups, guanidinium groups, imidazole groups, indole groups, purine groups, pyrimidine groups, pyrrole groups, etc.

In contrast, a polysaccharide containing a group ionizable at a high pH, e.g., capable of forming a negative charge (e.g., alkoxide groups, carboxyl groups, carboxylate groups, hydroxy acid groups, phenolic groups, phosphate groups, sulfhydryl groups, etc.) is attracted in its soluble state to the positive electrode and deposits on the positive electrode, but not the negative electrode. Accordingly, the electrically conductive support will be polarized to serve as the positive electrode for polysaccharides containing groups ionizable at a high pH.

Various aspects of the electrochemical cell, reaction conditions, and process parameters may be manipulated to control the chemical deposition on the electrically conductive support and the resulting properties and traits of the deposited polysaccharide mass. The physical state of the mass may be, for example, that of a solid compacted film, a semi-solid hydrogel, or a physical state between a compacted film and a hydrogel. Generally, reaction conditions and process parameters that have the greatest influence on physical state are the current density, pH, and deposition time. Other process conditions that may also influence the physical state of the deposition include the applied voltage, total ion concentration, polysaccharide concentration, temperature, and the like. Generally, high current densities and pH's relatively near the solubility limit are preferred for formation of hydrogels.

Other deposition techniques known in the art or otherwise suitable for the deposition of the reactive layer on the substrate may also be practiced.

(a)(ii)(D) Chitosan Deposition

An example of a method for controlling deposition conditions to form a chitosan film/gel mass with a selected physical state will now be explained in further detail with reference to the polysaccharide chitosan.

The electrodeposition of chitosan is accomplished by application of an electrical voltage between the deposition electrode (e.g., a patterned Au wire) and a counter electrode while chitosan is in its solubilized state. To solubilize chitosan into solution, an aqueous solution will have a pH less than about 6.3, e.g., 1 to 6.3. The chitosan solution used to deposit chitosan onto the support may have a chitosan content of, for example, about 0.0001 to about 0.001 weight percent (grams chitosan/grams solution), about 0.001 to about 0.01 weight percent, about 0.01 to about 0.1 weight percent, about 0.1 to about 1 weight percent, about 1 to about 10 weight percent, about 10 to about 20 weight percent, and about 20 to about 30 weight percent.

The operational electrical circuit may be controlled by using a controlled constant voltage, a controlled constant current, or a mixture of the two as the deposition proceeds. Using constant voltage there is typically a large current and high deposition rate until an initial chitosan deposit is achieved, after which the current is reduced by the series resistance of the chitosan. Using constant current, the initial voltage is typically small but then increases rather quickly to a nearly constant value as the resistive chitosan deposit develops on the surface.

From its soluble state, the chitosan deposition on the platform, i.e., the negative electrode, optionally can be controlled temporally and spatially based on when and where the voltage is applied, and the shape of the electrically conductive support. The tendency of the depositing chitosan to form a hydrogel (instead of a solid compact film) is increased with use of a pH at or near 6.3, e.g., about 5 to about 5.5, a relatively high current density, e.g., about 20 to about 100 A/m$^2$ (e.g., about 50 A/m$^2$), and a relatively high deposition time, e.g., about 2 to about 30 minutes. These variables are interdependent. For example, the tendency that a lower pH may have away from forming a hydrogel may be offset by use of a higher current density and/or deposition time.

Without wishing to be bound by any theory, proton consumption at the cathode surface is partially compensated for by proton generation from the dissociation of water. A pH gradient can be generated adjacent to the cathode surface, depending on the relative rates of hydroxyl ion generation and hydroxyl ion diffusion from the interface region. The generation of a pH gradient at the cathode surface is well established in electrochemical systems and has been used to explain the anomalous codeposition of metals. Dahms, H. et al., *J. Electrochem. Soc.*, 1965, 112, 771-775; Higeshi et al., *J. Electochem. Soc.*, 1981, 2081-2085; Hessami, et al., *AIChE J*, 1993, 39, 149-162; Paunovic et al., *Fundamentals of Electrochemical Deposition*, Wiley-Interscience (1998). A pH gradient is established in the immediate vicinity of the cathode surface when a voltage is applied to the electrodes. Depending upon the conditions, the insoluble chitosan chains can form a three-dimensional hydrogel network. It is believed that the hydrogel is deposited as a physical gel. The physical gel may be converted into a chemical gel, for example, by addition of crosslinkers (e.g., glutaraldehyde), which are discussed in further detail below.

The thickness of the deposited chitosan hydrogel may range, for example, from about 10 microns to about 10 millimeters, or more narrowly about 100 microns to about 5 millimeters. The concentration of the chitosan solution, the voltage and the time a current is applied to deposit chitosan onto a substrate can be varied to control thickness.

The tendency of the depositing chitosan to form a solid compact film is increased with use of a pH of about 5 to about 5.5, a relatively low current density, e.g., about 0.1 to about 10 A/m$^2$ (e.g., about 1 A/m$^2$ to about 5 A/m$^2$), and a relatively short deposition time, e.g., about 1 to about 10 minutes. For example, under typical conditions at a current density 2-5 A/m$^2$, the voltage rises within 1 min to slightly over 2 V and remains nearly constant over a total deposition time of 5 min. The deposition process is more reproducible and controllable for constant current mode of electro deposition of chitosan.

The thickness of the deposited chitosan solid compact film may range from tens of nanometers to micrometers, for example, from about 0.01 to about 3 microns, from about 0.01 to about 1.5 microns, or from about 0.02 to about 0.8 microns.

The deposited chitosan mass may possess a high amine group concentration. By estimate, the concentration of a chitosan hydrogel may range from $10^{24}$/m$^3$ to $10^{26}$/m$^3$ (e.g., $7 \times 10^{25}$ amine/m$^3$), preferably in a substantially homogeneous distribution. A deposited chitosan compact film may possess a high amine group concentration of about $10^{14}$-$10^{15}$/cM$^2$, e.g., $10^{14}$/cm$^2$, preferably in a substantially homogeneous distribution. The chitosan may include N-acetylglucosamine residues and/or blocks, preferably in a concentration of less than 40 weight percent, more preferably less than 30 weight percent.

(a)(ii)(E) Multiple Layers

In certain embodiments of the invention, the deposition conditions may be controlled to provide a substantially uniform hydrogel. In other embodiments, the deposition conditions may be controlled to provide a substantially uniform compact film.

According to another embodiment of the present invention, a method is provided for electrochemically depositing a polysaccharide deposit having a selected physical state, comprising: providing a substrate comprising a substrate surface, the substrate surface comprising an electrically conductive support; contacting the electrically conductive support with an aqueous solution comprising a selectively insolubilizable polysaccharide; and electrochemically depositing the selectively insolubilizable polysaccharide on the electrically conductive support while changing deposition conditions to form polysaccharide masses layered or otherwise arranged with respect to one another, each of the masses preferably possessing different physical and/or chemical properties in relation to adjacent layer(s).

The providing, contacting, and electrochemically depositing steps of this embodiment may be performed substantially as explained above with previous embodiments. However, deposition conditions are changed during electrochemical deposition to provide multiple (two or more) layers. For example, operating at a low current density of about 1-5 A/m$^2$ may allow for initial deposition of a compact polysaccharide film, after which the current density may be raised to, for example, about 50 A/m$^2$ to build a hydrogel layer on the compact polysaccharide film. Two, three, or more layers may be built upon one another in this manner. The interface (or transition) between adjacent layers may be made relatively distinct by rapidly and radically changing the deposition conditions. Alternatively, deposition conditions may be gradually altered during deposition to provide a subtle or blurred transition between adjacent layers.

(a)(ii)(F) Stabilization

In a preferred embodiment of the invention, the selectively insolubilizable polysaccharide mass deposited on the electrode(s) is stabilized (or destabilized) by pH adjustment, such as by washing the deposited polysaccharide with a liquid selected from water, a solution of neutral pH, a basic solution, and an acidic solution. In the case of a polysaccharide containing a group ionizable at a low pH, e.g., capable of forming a positive charge (e.g., amine groups), moderate increases to the pH above the pKa of the selectively insolubilizable polysaccharide will increase the insolubility of the deposited polysaccharide and improve stabilization, establishing a stable polysaccharide mass that optionally may be removed from the negative electrode. On the other hand, lowering the pH of the positively charged ionizable polysaccharide will lead to destabilization. In contrast, in the case of a polysaccharide containing a group ionizable at a high pH, e.g., capable of forming a negative charge (e.g., a carboxyl group), lowering the pH below the pKa of such selectively insolubilizable polysaccharide will improve stabilization, whereas raising pH will lead to instability.

For example, washing an acidic, soluble chitosan deposited mass with a base neutralizes and deprotonates the chitosan, converting the chitosan into an insoluble, stable hydrogel. Suitable bases include sodium hydroxide, ammonium and organic bases. The chitosan masses are stabilized by neutralization, permitting the chitosan to be retained on the electrode surface in the absence of an applied voltage. On the other hand, washing the chitosan deposited mass with an acid to lower the pH below the pKa will dissolve the mass.

Another form of stabilization that may be practiced comprises crosslinking, for example, with glutaraldehyde or transglutaminase. Crosslinking is discussed in greater detail below.

(a)(iii) Coating a Biologically Compatible Resist

A surface region of the reactive layer (e.g., polysaccharide mass) is coated with a biologically compatible resist. As referred to herein, surface region may encompass an entire surface of the reactive layer or less than the entire surface of the reactive layer.

The resist preferably is susceptible to modification, patterning, and removal, such as, for example, by thermal and/or enzymatic reaction. The resist of preferred embodiment of the invention is biologically compatible with the reactive layer and molecular species (if any) conjugated to the reactive layer, so that the reactive layer and any conjugated molecular species are not significantly adversely affected during modification, patterning, and removal of the resist. The biologically compatible resist preferably comprises an organic material or biomaterial. According to an embodiment, the resist is made of a material with stimuli responsive (e.g., thermally responsive) properties that permit the resist to be selectively removed (e.g., via thermal treatment) without adversely affecting the reactive layer and molecules (if any) conjugated to the reactive layer.

According to an embodiment of the invention, the resist comprises a thermally responsive protein gelatin cast over the surface region. Gelatin may be cast above its melt temperature, then allowed to cool at room temperature, e.g., for at least 15 minutes. Other techniques may be used for depositing the resist. Such deposition techniques include, for example, flowing, pouring, spin coating, etc., the gelatin precursor as a liquid. Such techniques are particularly useful for substrates comprising a bioMEMS device or environment. The flowed precursor liquid then is permitted to form, e.g., into a gel, at specific internal locations in the bioMEMS.

It is to be understood that other thermally responsive polymers may be selected as the thermoresist. Examples include proteins (e.g., collagen) polysaccharides (e.g., agar), elastin-like polypeptides, and synthetic polymers having thermally responsive properties, such as poly-N-isopropylacrylamide.

The thickness of the resist may range from, for example, about 0.1 mm to about 10 mm, such as about 1 mm.

(b) Selective Removal of Resist

Removal or dissolution of a selective portion of the resist preferably is performed by local heating or enzymatically, although other techniques (e.g., solubilization via, e.g., pH adjustment) may be practiced. In the examples below, pattern transfer is accomplished by a method comprising selective exposure of the underlying reactive layer (e.g., polysaccharide), said selective exposure comprising applying a heated stamp (thin wire) to melt specific regions of the gelatin thermoresist, and rinsing and removing the melting/melted regions. As an alternative to the application of a heat stamp to the exposed surface of the thermoresist, for example, stamps or heaters may be microfabricated and applied to the substrate. Stamps or heaters also may be fabricated directly into the substrate itself and selectively activated.

Selective thermal removal of the resist may be accomplished via techniques not requiring or making use of a heat stamp. For example, rapid, localized heating commonly used in semiconductor processing operations—such as graphoepitaxy, zone melting recrystallization, and pulsed laser annealing—may be used to thermally removed the resist and expose selective regions of the underlying reactive layer. Laser heating techniques, such as pulsed laser heating may be used for selectively removing a portion of the resist. Pulsed heating on a nanosecond time scale may increase spatial resolution, as observed in pulsed laser heating and ablation of materials. The transmission of optical energy to the desired sites, for example, within the bioMEMS can be accomplished either through transparent windows in the bioMEMS or via integrated optical waveguides from the package level outside the bioMEMS. The melted gelatin may then be washed away in the bioMEMS, such as by selective actuation of a microfluidic flow channel associated with the region of the melted gelatin.

Selective resist removal also may be accomplished via non-thermal techniques, used alone or in combination with thermal techniques. For example, the release by application of suitable enzymes (e.g., protease) or pH-adjusting medium (as in the case of chitosan discussed herein) onto the reactive layer may be performed. Release control by enzymes and pH-adjusting media in a bioMEMS environment may be accomplished via microdevices and microfluidic capabilities (e.g., fluid flow controls and delivery and exhaust pathways for the resist removal process). The microfluidic capability may also be used in conjunction with thermal heating, as in the case in which a bioMEMS systems is heated macroscopically or by internal microheaters to dissolve the resist (e.g., gelatin), which is then flushed from the bioMEMS by microfluidic flow.

These processes (e.g., thermal, enzymatic activation, pH control) selectively expose the underlying layer and create a pattern in the resist layer. For example, in the case of an applied stamp or the like, the process creates a negative image of the applied stamp in the resist layer. In the event the gelatin layer is selectively removed by contacting a heating device (e.g., a stamp) with the gelatin layer, the heating device is preferably withdrawn from the gelatin layer as the melted gelatin is cooling, but just before this layer completely gels. Premature withdrawal of the contacting heating device—i.e., before gel formation—may cause the gelatin solution to flow back and re-coat the exposed portion of the chitosan reactive sub-layer. Delayed withdrawal of the stamp—i.e., after gel formation—may cause the gelatin to adhere to the stamp, thereby resulting in tearing or delamination of the resist during withdrawal of the heating device. Corresponding considerations apply to the case where a macroscopic stamp is not employed, but rather microdevices (e.g., heaters, fluid flow controls) incorporated into the bioMEMS are used.

(c) Conjugation and Crosslinking

The spatially selective removal of the resist from specific locations on the reactive layer (e.g., the polysaccharide mass) exposes active sites of the reactive layer for conjugate bonding with other molecules. In this manner, the depositing and selective removal of the resist from selected locations of the active layer is analogous to lithographic patterning, that is, biolithography using biological materials as a resist.

Examples of molecules that may be bonded to the exposed portions of the reactive layer include biomolecular and/or cellular species (eukaryotic or prokaryotic). Examples of biomolecular species include proteins (especially enzymes, receptors, receptor ligands, and antibodies), nucleic acid molecules (especially DNA and RNA), antigens, polysaccharides, drugs (e.g., opiates, cannabinoids, etc.), etc. Examples of cellular species include whole cells (e.g., such as cultured or primary human, non-human mammalian, insect, yeast, fungal or other eukaryotic cells, or bacterial cells) or sub-cellular components thereof, viruses or sub-viral components thereof. As used herein, the terms sub-cellular and sub-viral components are intended to refer to membrane-associated proteins (especially enzymes, receptors, and receptor ligands), membrane-associated antigens, organelles, etc. The binding of such biomolecular and/or cellular species is particularly amenable for use in microfluidic systems. The reactive layer (e.g., polysaccharide mass) of the present invention may be modified to facilitate its ability to stably conjugate with other molecules. Additionally or alternatively, the other molecules may be modified to facilitate their ability to stably conjugate with the reactive layer (e.g., the polysaccharide mass).

Such modifications may include covalent cross-linking agents (e.g., dialdehydes (such as glutaldehyde, formaldehyde, glyoxal, etc.), anhydrides (such as succinimide, carbodiimide, dicyclohexylcarbodiimide, etc.), genipin, amino acids, etc.) or non-covalent crosslinking agents (such as tripolyphosphate (TPP), etc.). In one embodiment, such molecules will be nonspecifically divalent or multivalent, possessing two or more identical reactive groups that can be used to conjugate the polysaccharides of the reactive layer to other molecules (e.g., glutaraldehyde, lysine, arginine, glutamate, aspartate, polysaccharides, etc.) so as to provide "spacer" molecules that can address and diminish potential issues of steric interference. In another embodiment, such molecules will comprise two or more different relevant reactive groups such that an orthogonal synthetic approach may be employed. Examples of such compounds include amino acids. The carboxyl group of such compounds can be conjugated to the amine group of, for example, chitosan, to yield a free, and more sterically accessible, amino group that can be conjugated to the carboxy group of a glutamate or aspartate residue of a protein. Likewise, the reactive layers of the present invention can be modified to contain chloromethylbenzyl or trialkylsulfoniumbenzyl groups that can then react with the carboxyl group of other molecules.

Modifications may optionally be conducted enzymatically. Any of a variety of enzymes may be used for this purpose. Such enzymes may be used to activate a chemical group of a protein or other ligand so as to facilitate its reaction with a chemical group of the reactive layer. For example, without wishing to be bound by theory, it is believed that such enzymes activate phenols (such as tyrosyl residues of proteins, such as green fluorescent protein (GFP)) to convert the phenols to quinones. The activated quinones can then react with nucleophilic substituents, such as nucleophilic substituents of chitosan. Such enzymes are readily available commercially, and are ubiquitous in natural sources. For example, tyrosinase enzymes, phenol oxidases, and polyphenol oxidases (also peroxidase enzymes and probably laccase enzymes) may be employed to react with the tyrosine residues of a protein so as to facilitate the covalent bonding of the tyrosine phenolic oxygen to an amine group of chitosan.

The specific activity of the enzyme used will determine how much of the enzyme should be added. As an illustration, for a mushroom tyrosinase enzyme, a convenient level is from about 1 to about 200 U/mL, preferably about 20 to about 100 U/mL, and most preferably about 60 U/mL. Higher amounts of enzyme content may result in depletion of the phenolic compound or molecular oxygen in the solution. The reaction is then allowed to proceed, conveniently with stirring overnight.

Owing to the flexibility of the chemistry involved, any of a wide variety of different compounds can be conjugated to the polymer. Such compounds particularly include proteins (especially enzymes, receptors, receptor ligands, or antibodies) and nucleic acid molecules (especially DNA or RNA).

For example, chitosan possesses amino groups that confer nucleophilic properties to the polymer. Specifically, the deprotonated amino groups have an unshared electron pair that can undergo reaction with a variety of electrophiles. As a result, various chemistries can be exploited to crosslink chitosan and to graft (or conjugate) substituents onto the polymer. The substituent may be coupled to the chitosan before and/or after the chitosan has been deposited onto the substrate. The substituent may comprise various molecules, such as labile biomolecules. Such biomolecules include, not necessarily by limitation, bound proteins, enzymes, polynucleotides, RNA, DNA, cells, and the like. The molecules are assembled on the polysaccharide template, which acts as an interface between the molecules and the inorganic substrate.

The reactive layer can be used to provide two-dimensional surface or three-dimensional matrix for molecular interactions. The surface or matrix may be spatially and/or temporally defined by selective removal of the resist.

In one embodiment, the conjugated molecules of such surfaces or matrices will comprise one, two, three or more enzyme species. Significantly, by incubating such surfaces or matrices in contact with a fluidic layer (i.e., a surface or matrix that contains a flowing or flowable liquid or gas capable of transporting other molecules (e.g., nucleic acid molecules, proteins, enzymatic substrates and/or products, etc.)), multiple stepwise synthetic reactions can be made to occur, either sequentially or in parallel. Suitable enzyme species include: aminopeptidases, angiotensin converting enzymes, caspases, cathepsins, cholinesterases, collagenases, deaminases, endonucleases, endopeptidases, esterases, exonucleases, lipases, nucleotidases, phosphatases, proteases, restriction endonucleases, etc.

In a second embodiment, the conjugated molecules of such surfaces or matrices will comprise one, two, three or more antibody species. As used herein, the term "antibodies" is intended to encompass not only conventional immunoglobulins, but also single chain antibodies, humanized antibodies, monoclonal antibodies, etc. Significantly, by incubating such surfaces or matrices in contact with a fluidic layer containing antigens, multiple immunoassays can be simultaneously or sequentially conducted. Any of a wide variety of assay formats may be used in accordance with the methods of the present invention. They may be heterogeneous or homogeneous, and they may be sequential or simultaneous. They may be competitive or non-competitive. U.S. Pat. Nos. 5,563,036; 5,627,080; 5,633,141; 5,679,525; 5,691,147; 5,698,411; 5,747,352; 5,811,526; 5,851,778 and 5,976,822 illustrate several different assay formats and applications.

In a third embodiment, the conjugated molecules of such surfaces or matrices will comprise one, two, three or more bound receptor molecule species or bound ligands of receptor molecules. Significantly, by incubating such surfaces or matrices in contact with a biological sample, multiple receptor/receptor ligand binding assays can be simultaneously or sequentially conducted. Suitable receptor species include: 5-hydroxytryptamine receptors, acetylcholine receptors, adenosine receptors, adrenoceptor receptors, adrenomedullin receptors, amylin receptors, amyloidreceptors, angiotensin receptors, atrial natriuretic peptide (ANP) receptors, bombesin receptors, bradykinin receptors, calcium-channel receptors, cannabinoid receptors, cgrp receptors, chemokine receptors, cholecystokinin and gastrin (CCK) receptors, corticotropin releasing factor (CRF) receptors, dopamine receptors, endothelin receptors, excitatory amino acid receptors, gaba receptors, galanin receptors, gastric inhibitory peptide (GIP) receptors, GDNF receptors, glucagon receptors, glucagon-like peptide receptors, glycoprotein hormones receptors, growth hormone secretagogue receptors, GTP-binding-protein receptors, hemotopoietin receptors, histamine receptors, imidazole receptors, integrin receptors, interleukin-1 receptors, melanin-concentrating hormone receptors, melanocortin receptors, melatonin receptors, metastin receptors, motilin receptors, neuromedin receptors, neuropeptide FF receptors, neuropeptide Y receptors, neurotensin receptors, opioid receptors, orexin receptors, P2 purinoceptor receptors, parathyroid hormone (PTH) receptors, phosphodiesterase enzyme, platelet activating factor (PAF) receptors, potassium-channel receptors, prolactin receptors, prostanoid receptors, retinoid receptors, selectin receptors, somatostatin receptors, steroid receptors, tachykinin receptors, tumour necrosis factor (TNF) receptors, tyrosine kinase receptors, urotensin II receptors, vasoactive intestinal peptide (VIP) receptors, vasopressin receptors, etc.

In a fourth embodiment, the conjugated molecules of such surfaces or matrices will comprise one, two, three or more bound nucleic acid molecule species, which may be DNA or RNA or be composed of non-naturally occurring residues (e.g., PNA). Such nucleic acid molecules may have defined sequences (such as the sequences of genes or fragments thereof), or may be composed of random or pseudorandom oligonucleotides (i.e., nucleic acid molecules of 3-100 nucleotides in length) or polynucleotides (i.e, nucleic acid molecules greater than 100 nucleotides in length). Significantly, by incubating such surfaces or matrices in contact with a biological sample (or an extract thereof), multiple hybridization reactions involving nucleic acid molecules present in the sample can be simultaneously or sequentially conducted.

Such hybridization reactions can be used in concert with nucleic acid amplification strategies (such as the polymerase chain reaction (PCR) (e.g., U.S. Pat. Nos. 4,683,202; 4,582,788; U.S. Pat. Nos. 4,683,194, 6,642,000, etc.)); ligase chain reaction (LCR), self-sustained sequence replication (3SR) (e.g., Guatelli et al., Proc. Natl. Acad. Sci. USA 87:1874-1878 (1990); PCT Publication. WO 88/10315), nucleic acid sequence based amplification (NASBA) (e.g., Kievits, J Virol Methods. 35:273-86 (1991)), strand displacement amplification (SDA) (e.g., U.S. Pat. No. 5,270,184), and amplification with Qβ replicase (Birkenmeyer et al., J. Virological Methods, 35:117-126 (1991); Landegren, Trends Genetics, 9:199-202 (1993); and rolling circle amplification (e.g., U.S. Pat. Nos. 5,854,033; 6,183,960; 5,354,668; 5,733,733)) to accomplish the amplification of the hybridized molecules, or their complements. The present invention permits hundreds, thousands, and tens of thousands of nucleic acid species to be deposited on to such surfaces or matrices.

Additionally, such hybridization reactions may be used to sequence the nucleic acid molecules present in the sample, or to assess the expression profile of the genes of cells present in the biological sample (or an extract thereof) (see, e.g., U.S. Pat. Nos. 6,632,606; 5,002,867; 5,202,231; 5,888,819; Lipshutz et al., Biotechniques, 9(3):442-447 (1995) and Chee et al., Science, 274:610-614 (1996); DeRisi, J. et al. (1996) "USE OF A cDNA MICROARRAY TO ANALYSE GENE EXPRESSION PATTERNS IN HUMAN CANCER" *Nature Genetics* 14:457-60; Luo, L. et al. (1999) "GENE EXPRESSION PROFILES OF LASER-CAPTURED ADJACENT NEURONAL SUBTYPES" *Nature Medicine* 5:117-22; Bonner, R. F. et al. (1997) "LASER CAPTURE MICRODISSECTION: MOLECULAR ANALYSIS OF TISSUE" *Science* 278:1481, 1483; Schena, M. et al. (1995) "QUANTITATIVE MONITORING OF GENE EXPRESSION PATTERNS WITH A COMPLEMENTARY DNA MICROARRAY" *Science* 270:467-70).

In a fifth embodiment, the conjugated molecules of such surfaces or matrices will comprise one, two, three or more non-ionizable polysaccharides or other polymer molecules. Thus, for example, the present invention permits one to accomplish the spatial and/or temporal selective deposition of polymers such as: aramids, celluloses, kevlars, nomex, nylons, poly(ether sulfone)s, poly(methyl methacrylate)s, poly(phenylene oxide)s, poly(phenylene sulfide)s, poly(vinyl acetate)s, poly(vinyl chloride)s, poly(vinyl) fluorides, poly (vinylidene chloride)s, poly(vinylidene fluoride)s, polyacrylonitriles, polybutadienes, polycarbonates, polychloroprene, polycyanoacrylates, polydicyclopentadienes, polyesters, polyethylenes, polyimides, polyisobutylenes, polyketones, polypropylenes, polystyrenes, polytetrafluoroethylenes, polyurethanes, polyvinylpyrrolidones, rayons, silicones, starches, etc.

(d) Removal of Resist

In some instances, the resist may be removed from the underlying reactive layer by melting or dissolution. For example, meltable gelatin may be melted and dissociated from the reactive layer by immersing or otherwise contacting the gelatin thermoresist in/with warm water. The temperature of the water and contact time may be adjusted based on the melting temperature of the resist. Other techniques may be used for resist removal, include enzymatic treatment.

In other instances, the gelatin may become crosslinked due to the introduction of crosslinkers to the underlying reactive layer. To remove the gelatin resist under these circumstances without destroying either the reactive layer or its conjugated molecules, a protease may be used.

The microfluidic capabilities of a bioMEMS environment may comprise delivery and exhaust pathways for accomplishing the resist removal process. For example, the bioMEMS environment may be heated macroscopically or via internal microheaters to dissolve the resist, which then can be flushed from the bioMEMS via microfluidic flow. The bioMEMS environment may also comprise microfluidic capabilities for allowing the introduction of enzymes (e.g., protease, etc.) or other agents for the dissolving and removing the resist.

Exemplary Applications

It is contemplated that the deposited materials and methods of the present invention may be used and practiced in various settings and environments and as components for various devices, including, for example, biosensors, microarrays, micro electromechanical systems (MEMS), and complex, multi-site biomicrofluidic applications and associated multi-step biochemical reaction sequences.

The methods and materials of embodiments of the present invention provide various combinations of benefits and advantages when used in MEMS and similar devices for several reasons. First, the fabrication technique is relatively simple to practice. Expensive equipment (e.g., pin printers) and facilities (e.g., clean rooms) are not needed for thermo-biolithography. The reactive layer and resist layer are easily coated on the substrate, while facile procedures can be used to conjugate molecules. Second, pattern transfer and resist removal may be achieved under mild, bio-friendly conditions. Third, the use of biopolymers, enzymes, and/or aqueous solvents in embodiments of the present invention may provide safer and more environmentally friendly alternatives to existing fabrication methods. Further, the resultant products may be biodegradable. Fourth, devices fabricated using certain resists (e.g., gelatin) and reactive layers (e.g., chitosan) may have end-use applications in medicine, such as drug delivery and artificial organs, because both biopolymers are considered biocompatible.

The following examples serve to explain and elucidate the principles and practice of the present invention further. These examples are merely illustrative, and not exhaustive as to the scope of the present invention.

EXAMPLES

Chitosan from crab shells (85% deacetylation and 370,000 molecular weight as reported by the manufacturer), gelatin (type A from porcine skin, approximately 175 Bloom), phosphate buffered saline tablets (PBS), Tris-EDTA buffer (100× concentrate), sodium dodecyl sulfate, glutaraldehyde (grade I, 50% w/w aqueous solution), urea (SigmaUltra grade), proteinase-K enzyme from *Tritirachium album* (47 U/mg), tyrosinase from mushroom (6680 U/mg), dimethylformamide (DMF), sodium hydroxide and ethanol (100%), were all purchased from Sigma Chemicals. The fluorescent probes 5-(and 6-)-carboxyfluorescein succinimidyl ester (NHS-fluorescein) and 5-(and 6-)-carboxytetraniethylrhodamine succinimidyl ester (NHS-rhodamine) were both purchased from Molecular Probes. Twice-HPLC-purified amine-terminated, fluorescently-labeled ssDNA of 20 bases from the dnaK genes of *Escherichia coli* were purchased from Gene Probe Technologies.

Details on the preparation of chitosan solutions as well as the fabrication of gold-coated wafers have been described in PCT/US03/40801 entitled "Spatially Selective Deposition of Polysaccharide Layer onto Patterned Template," filed Dec. 19, 2003. The description of these preparatory steps is reproduced below. [Silicon wafers with 1 μm thick thermal oxide film (four inch diameter) were obtained from MEMC Electronic Materials. The gold and chromium used for sputtering onto the wafer were purchased from Kurt J. Lesker Co. The primer was hexamethyldisilazane (HMDS, Microelectronic Materials). The photoresist (Microposit Photoresist S1813) and developer (Microposit Developer 352) were purchased from Shipley Co. The etchants (TFA for gold and TFD for chromium) were obtained from Transene Co.

[Chitosan solutions were prepared by adding chitosan flakes to water and incrementally adding small amounts of HCl to the solution to maintain the pH near 3. After being mixed overnight, the chitosan solutions were filtered to remove undissolved material, and the pH of the solution was adjusted using NaOH (1 M).

[The patterned electrically conductive substrate surfaces were fabricated by depositing 150 Angstrom thick chromium and then 2000 Angstrom thick gold films on 4-inch diameter silicon wafers, which had previously been coated with 1 μm thick thermal oxide film. Patterning was achieved using photolithography in which a primer and then photoresist were spin-coated onto the gold surface. After soft-backing the coated wafer at 100° C. for 1 min, a specially designed mask was placed over the surface and the wafer was exposed to UV light (total dosage ~190 mJ/cm$^2$). After 30 seconds of development, the wafer was then hard-baked at 120° C. for 10 min. The exposed areas were then etched away by gold and chromium etchants, and the photoresist was removed using acetone.]

The protocol for the preparation of the fusion protein: Green Fluorescent Protein (GFP) with 6 histidine residues at its N-terminus and 5 tyrosine residues at its C-terminus (His)$_6$-GFP-(Tyr)$_5$ has also been described in earlier work. See Chen, T., et al., *Langmuir*, in press; U.S. provisional application No. 60/446,978 filed in the U.S. Patent & Trademark Office on Feb. 12, 2003 entitled "Nature-Inspired Creation of Protein-Polysaccharide Conjugate; and PCT/US04/03878 filed Feb. 11, 2004, entitled "Controlled Electrochemical Deposition of Polysaccharide Films and Hydrogels, and Materials Formed Therefrom."

To prepare, 1 μg/ml of the GFP-solution, the concentrated protein solution was diluted using PBS. Gelatin solutions (15% w/w, pH=7.5) were prepared by dissolving the required amount of gelatin to coat the chitosan in double-distilled water (DDW) at temperatures above 50° C. The pH was adjusted to 7.5 using small amounts of 1 M NaOH. PBS buffer was prepared by dissolving PBS tablets in DDW and adjusting the pH to 7.4. Tris-EDTA-SDS buffer was prepared by adding sodium dodecyl sulfate (SDS) to Tris-EDTA so as to have 0.5% w/w SDS in the resulting solution. The 0.025% w/w glutaraldehyde solution was prepared by diluting the 50% w/w aqueous glutaraldehyde with PBS buffer. The 4 M urea solution was prepared by dissolving the urea pellets in DDW. Proteinase-K enzyme solution was prepared by dissolving 1 mg proteinase-K in 10 ml of Tris-EDTA-SDS buffer. Tyrosinase enzyme solution (2000 U/ml) was prepared by dissolving tyrosinase in DDW. NHS-fluorescein and NHS-rhodamine solutions were both prepared by first dissolving these compounds in 200 μL dimethylformamide and then adding 800 μL of ethanol. These fluorescein solutions were added drop-wise to PBS buffer to create the final reaction mixture.

Initial studies with NHS-fluorescein were performed using a glass microscope slide as the substrate. Nucleic acids and proteins were patterned using smaller substrates to limit the consumption of the reagents. Silicon wafer "chips" or substrates were selected for these studies because of their ease of preparation. Furthermore, these 'chips' were gold-coated to facilitate heat transfer during the thermal pattern transfer step. The chitosan sub-layer was prepared by spreading the acidic chitosan solution (2% w/w) onto the surface of the substrate and then immersing the substrate in base (1 M aqueous NaOH) to neutralize the chitosan. Chitosan is insoluble above a pH of about 6.5. The resulting chitosan reactive layer was washed extensively with DDW to remove traces of any salts formed during the neutralization and then air-dried. The gelatin thermoresist was cast on top of the chitosan reactive layer by spreading the gelatin solution (15% w/w at 50° C.) and allowing it to air cool for 15 minutes. The stamps used for thermo-biolithography consisted of 0.6 mm-wide blades used either individually or as a pair separated by a spacer. The blades were heated on a hot plate to 50° C. prior to stamping. Photographs were taken at the end of each study using a fluorescence stereomicroscope (MZ FLIII, Leica) with the GFP1 filter for green fluorescent protein, the GFP2 filter for fluorescein, or the 41004 TXRD filter for rhodamine. The GFP1 filter consisted of an excitation filter at 425 nm (band width of 60 nm) and an emission barrier filter at 480 nm. The GFP2 filter consisted of an excitation filter at 480 nm (band width of 40 nm) and an emission barrier filter at 510 nm. The 41004 TXRD filter consisted of an excitation filter at 560 nm (band width of 40 LP nm) and an emission barrier filter at 610 nm.

Example 1

Initial experiments were performed to demonstrate the concept of thermo-biolithography—that gelatin can be exploited as a temperature-responsive, sacrificial barrier (thermoresist) for the spatially selective patterning of an underlying sub-layer. A glass slide was coated with a thin chitosan "reactive" sub-layer (estimated thickness was 1 μm or less) and then a thicker gelatin resist layer (~1 mm thick). The gelatin layer was allowed to gel by cooling at room temperature for 15 minutes. To transfer the pattern through the thermally sensitive gelatin resist, a stamp heated to 50° C. was applied to the surface of the gelatin. The stamp consisted of two metallic blades clamped together and separated by a spacer (blades were approximately 0.6 mm wide and were separated by 4 mm). The heated stamp melted through the gelatin resist until it came in contact with the underlying chitosan reactive sub-layer. Some gelatin in the vicinity of the stamp also melted while the chitosan sub-layer was unaffected by this thermal treatment. The stamp was held in place for several minutes to allow the melted gelatin to cool and reform a gel. The stamp was withdrawn from the gelatin layer just before this layer completely gelled. The timing for withdrawing the stamp was determined by manually probing the gelatin surface (with a spatula) to assess its elasticity. The timing of stamp withdrawal was important in this example. It was determined that premature withdrawal of the stamp—i.e., before gel formation—would cause the gelatin solution to flow back and re-coat the exposed portion of the chitosan reactive sub-layer. On the other hand, delayed withdrawal of the stamp—i.e., after gel formation—would cause the gelatin to adhere to the stamp and the resist would be torn and partially delaminated during stamp withdrawal.

As illustrated in FIG. 1, the next step was to react the exposed reactive chitosan sub-layer, while the gelatin resist protects the unexposed portions of the sub-layer. In Example 1, the slide was exposed to a fluorescent dye with amine-reactive functionality. Specifically, we immersed the slide in a Petri dish containing 1.6 μg/ml NHS-fluorescein in 50 ml of PBS buffer (pH=7.4) for 10 minutes. After reaction, the glass slide was recovered and rinsed extensively with water. Both the gelatin resist and the chitosan sub-layer were fluorescently-labeled by this amine-reactive reagent.

The next step illustrated in FIG. 1 was to remove the thermoresist. This was achieved by melting/dissolving away the gelatin layer by immersing the slide for 10 seconds in 1 liter of warm water (50° C.). The time and temperature for resist removal was adjusted based on gelatin's melting temperature, which depended on gelatin's type and concentration. After removing the gelatin, the glass slide was rinsed with water and stored in PBS buffer.

Figure 5A:
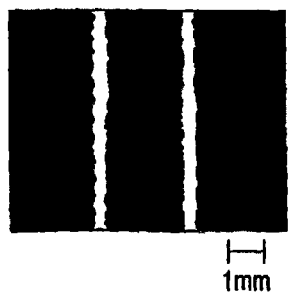
FIGS. 5A and 5B show a photomicrograph and a graph, respectively, associated with Example 1 described below. The fluorescence photomicrographs of patterned fluorescein bands were taken using an excitation filter of 480 nm (bandwidth 40 nm), an emission barrier filter of 510 nm and exposure time of 90 seconds.
Figure 5B:
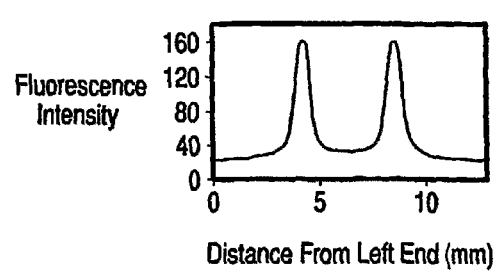

FIG. 5A shows a fluorescence photomicrograph of the glass slide after removal of the gelatin resist. As seen in FIG. 5A, there are two fluorescent bands, each approximately 0.6 mm in width spaced approximately 4 mm apart. These dimensions match the dimensions of the stamp used for the thermo-biolithography. To quantify patterning, the fluorescence intensity profile from FIG. 5A was analyzed. FIG. 5B shows a high fluorescence signal for the regions of the chitosan sub-layer that were exposed by thermo-biolithography. In contrast, the regions of the sub-layer that were protected by the gelatin thermoresist had low fluorescence intensity. The size and shape of the two peaks in FIG. 5B indicate that the thermo-biolithographic pattern transfer is reproducible.

Example 2

Nucleic Acids and Proteins

FIG. 6A illustrates a thermo-biolithographic approach for patterning nucleic acids, as carried out in Example 2. The substrate for these studies was a small rectangular "chip" (8 mm×20 mm) that had been cut from a gold-coated silicon wafer. A chitosan sub-layer, and then a gelatin resist layer were coated onto the chip and pattern transfer was performed as described above in Example 1. After pattern transfer, the exposed sub-layer was activated for nucleic acid conjugation by immersing the chip for 30 minutes in 5 ml of a PBS buffer solution containing 0.025% w/w glutaraldehyde, i.e., a homobifunctional amine-reactive crosslinking agent. After glutaraldehyde activation, the chip was rinsed extensively with PBS buffer to remove unreacted glutaraldehyde.

Figure 6B:
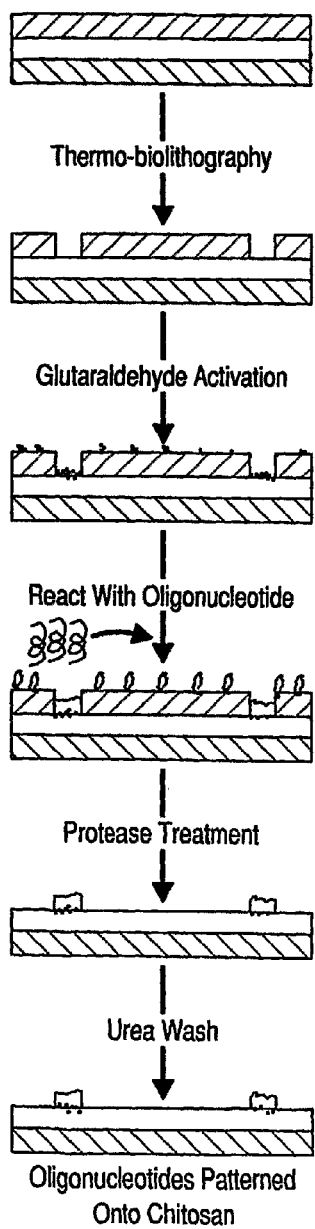
FIGS. 6B, 6C, and 6E show fluorescence photomicrographs associated with Example 2. All photomicrographs were taken using an excitation filter of 480 nm (bandwidth 40 nm), an emission barrier filter of 510 nm, and an exposure time of 60 seconds.
Figure 6B:
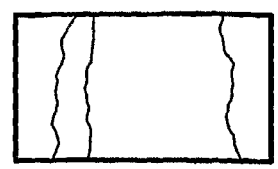

For nucleic acid coupling, the activated chip was placed in a 2 ml centrifuge tube with 1.5 ml of a PBS buffer containing 20 μg/ml of a fluorescently labeled, amine-terminated oligonucleotide. The model oligonucleotide was a 20-base sequence from the *Escherichia coli* dnaK gene. The coupling reaction was performed for 2 hours with mild agitation. After reaction, the chip was removed and rinsed extensively with PBS buffer. FIG. 6B shows a fluorescence photomicrograph of this chip after reaction and rinsing. As seen, the fluorescently labeled oligonucleotide is coupled both to the exposed chitosan sub-layer and the gelatin resist.

As illustrated in FIG. 6A, the next step is to remove the sacrificial gelatin resist. This resist could not be removed by simply dipping the chip in warm water because glutaraldehyde, which is used to activate the exposed chitosan sub-layer, also crosslinks gelatin and eliminates its ability to be melted or dissolved. To remove the crosslinked gelatin (protein) resist without destruction of either the conjugated nucleic acid or the chitosan polysaccharide sub-layer, a protease was used. Specifically, the chip was placed in a Petri dish with 5 ml of a Tris-EDTA-SDS buffer containing 100 μg/ml proteinase-K. To completely digest the gelatin, the chip was incubated in this solution with mild agitation for 6 hours at room temperature. After digestion, the chip was rinsed extensively with PBS buffer and examined using a fluorescence microscope. The fluorescence photomicrograph of FIG. 6C shows two 0.6 mm-wide bands spaced 4 mm apart.

Figure 6C:
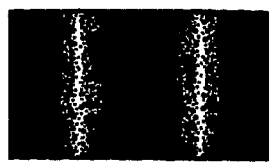
Figure 6D:
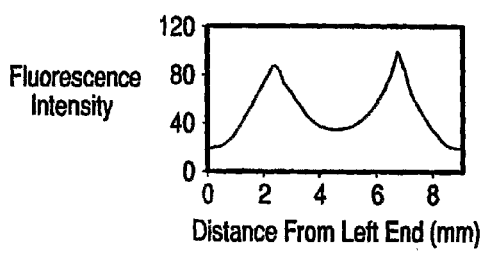
FIGS. 6D and 6F show fluorescence intensity profiles associated with the fluorescence photomicrographs of FIGS. 6C and 6E, respectively.
Figure 6E:
Figure 6F:
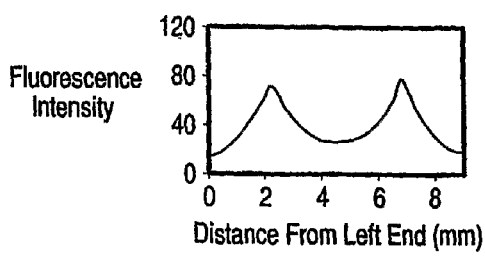

Image analysis of the fluorescence intensity of FIG. 6C is shown in FIG. 6D. As seen, higher fluorescence is observed in the regions where the chitosan sub-layer was exposed compared to the region protected by the gelatin thermoresist. To remove any physically bound oligonucleotides, we next immersed the chip in a 4 M urea solution for 1 hour at 50° C. with mild agitation. FIGS. 6E and 6F respectively show a fluorescence photomicrograph and corresponding fluorescence intensity profile for this chip after the urea wash. As can be seen, the urea wash had a relatively small effect on the images and the shapes of the intensity profiles of the patterned surface. This result shows that the fluorescently labeled oligonucleotide was covalently bonded to the exposed chitosan sub-layer. The similarity in size and shape of the two peaks in FIG. 6F illustrates the reproducibility of thermo-biolithographic patterning.

Comparative Example A

Figure 6G:
FIG. 6G shows a fluorescence photomicrograph associated with Comparative Example A. The photomicrograph was taken using an excitation filter of 480 nm (bandwidth 40 nm), an emission barrier filter of 510 nm, and an exposure time of 60 seconds.

As a control, a chip was prepared as illustrated in FIG. 6A except the sample was not activated with glutaraldehyde. This "control" chip was also treated with fluorescently labeled, amine terminated oligonucleotide solution. After removal of the gelatin with protease and performing the urea wash, the chip was examined using a fluorescence microscope. FIG. 6G shows that no image is observed in the fluorescence photomicrograph of this control. This result indicates that glutaraldehyde activation was necessary in this example for coupling of the fluorescently labeled, amine-terminated oligonucleotides.

The results of Example 2 and Comparative Example A demonstrate that thermo-biolithography can be combined with glutaraldehyde-based coupling chemistries for the patterning of oligonucleotides onto surfaces.

Example 3

Nucleic Acids and Proteins

Figure 7:
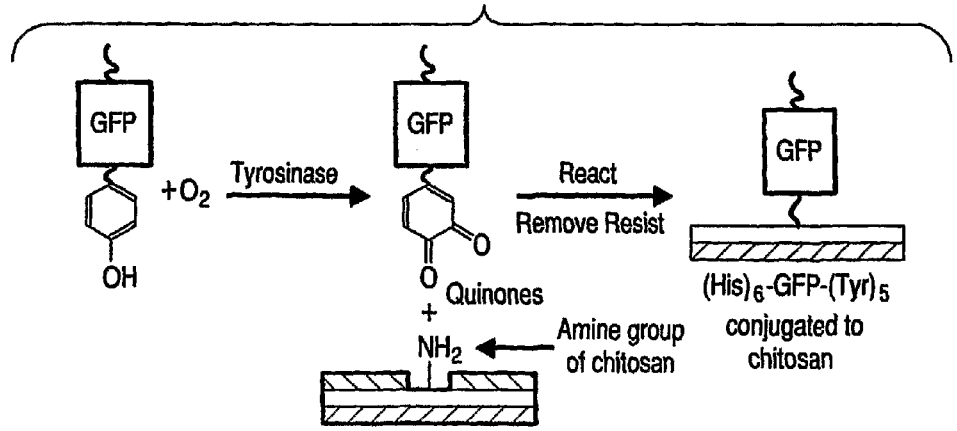
FIG. 7 shows a thermo-biolithographic approach for enzyme-initiated conjugation of proteins onto the exposed reactive sub-layer according to an embodiment of the invention, as carried out in Example 3.

FIG. 7 shows that protein patterning was achieved using an enzyme-initiated method to conjugate proteins onto the exposed chitosan sub-layer. The substrate and pattern transfer steps were the same as those used for oligonucleotide patterning. Protein conjugation was initiated by the enzyme tyrosinase that converted accessible tyrosine residues of the protein into reactive o-quinone residues capable of undergoing coupling reactions with chitosan. The protein was a fusion of green fluorescent protein with an N-terminus hexahistidine tag and a C-terminus pentatyrosine tag (($His)_6$-GFP-$(Tyr)_5$).

Figure 8A:
FIGS. 8A and 8C show shows fluorescence photomicrographs associated with Example 3 and Comparative Example B, respectively. Both fluorescence photomicrographs were taken using an excitation filter of 425 nm (bandwidth 60 nm), an emission barrier filter of 480 nm, and an exposure time of 15 seconds.

After thermo-biolithographic pattern transfer, the chip was dipped into 1.5 ml of a concentrated tyrosinase solution (2000 U/ml in a 2 ml centrifuge tube) for 30 minutes. This step served to "coat" the patterned chip with the tyrosinase coupling catalyst. In a second dip step, the chip was immersed in a 2 ml centrifuge tube containing 1.5 ml of a PBS buffer containing $(His)_6$-GFP-$(Tyr)_5$ (1 µg/ml). After a 2-hour incubation, the chip was recovered, washed extensively with PBS buffer, immersed in warm water (50° C. for 60 seconds) to remove the gelatin thermoresist, and then extensively washed with PBS buffer. It should be noted that tyrosinase can react with the small number of tyrosine residues of gelatin, but these reactions do not prevent gelatin from melting. The fluorescence photomicrograph of FIG. 8A shows two 0.6 mm-wide fluorescent bands spaced 4 mm apart. The fluorescence intensity profile in FIG. 8B further illustrates that tyrosinase can initiate the conjugation of GFP onto the exposed chitosan surface and that the patterning is reproducible.

Comparative Example B

Figure 8C:
Figure 8B:
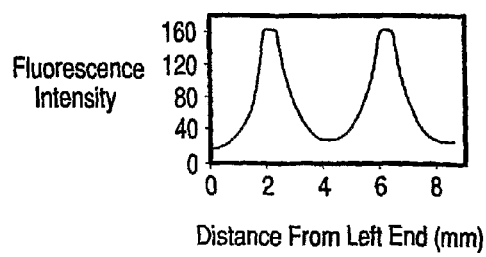
FIG. 8B shows a fluorescence intensity profile of a region photographed in FIG. 8A.

As a control, we performed thermo-biolithography and dipped the chip in the GFP-containing solution as described above, except the chip was not dipped in tyrosinase. The fluorescence photomicrograph of this control is shown in FIG. 8C and illustrates that very little fluorescence appears in this image. Thus, the results in FIGS. 8A to 8C demonstrate that proteins can be patterned onto chitosan surfaces using a combination of thermo-biolithography and tyrosinase-initiated conjugation.

Examples 4 and 5

Sequential Thermo-Biolithography

Examples 4 and 5 were prepared to demonstrate that sequential thermo-biolithographic steps could be performed to spatially pattern different species onto a surface.

In Example 4, two amine-reactive fluorescent dyes were patterned using the procedure illustrated in FIG. 9A. In the first pattern transfer step, a single 0.6 mm wide line was transferred through the gelatin resist using one blade. After pattern transfer, this glass slide was reacted with NHS-fluorescein and then the gelatin resist was removed using warm water. As expected, a 0.6 mm-wide line was visible when the slide was examined using a fluorescence microscope. For the second thermo-biolithographic step, the glass slide was once again coated with gelatin resist after which a 0.6 mm wide line was transferred through the gelatin resist. This second line was patterned to be parallel to the first. After this second pattern transfer step, the slide was placed in a Petri dish with 50 ml of PBS buffer (pH=7.4) containing 1.6 µg/ml NHS-rhodamine. After allowing the reaction to proceed for 10 minutes, the slide was recovered, rinsed, and the thermoresist was removed with warm water. At the end of the experiment, the chitosan sub-layer had been patterned to have one fluorescein band and a second rhodamine band spaced approximately 4 mm apart.

To visualize the images transferred during this sequential patterning operation, fluorescence photomicrographs were obtained using two different filters—one for each dye. The upper photograph in FIG. 9B shows the fluorescein band on the left, while the lower photomicrograph shows the rhodamine band on the right (the two bands could not be imaged simultaneously using our filter sets). Both bands in FIG. 9B are 0.6 mm-wide. This result provides evidence that thermo-biolithography can be performed sequentially to pattern multiple compounds to chitosan.

Figure 10A:
FIG. 10A shows a second approach for an embodiment comprising sequential thermo-biolithography, as carried out in Example 5.
Figure 10A:
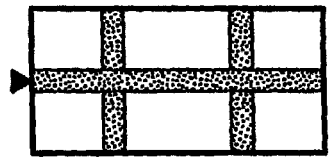
Figure 10B:
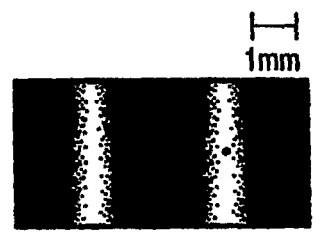
FIG. 10B shows a fluorescence photomicrograph and a fluorescence intensity profile after a first patterning step of the second approach of FIG. 10A. GFP images were obtained using an excitation filter of 425 nm (bandwidth 60 nm), an emission barrier filter of 480 nm, and an exposure time of 10 seconds.

Example 5 demonstrates that sequential thermo-biolithography can be performed with proteins. The schematic in FIG. 10A shows that the first patterning was performed to create two parallel bands of $(His)_6$-GFP-$(Tyr)_5$. Pattern transfer, tyrosinase-initiated conjugation, and resist removal were achieved as described above. FIG. 10B shows the fluorescence photomicrograph and the fluorescence intensity profile after this first patterning.

Figure 10C:
FIGS. 10C and 10D show fluorescence photomicrographs and a fluorescence intensity profile after a second patterning step of the second approach of FIG. 10A. The rhodamine band was observed using an excitation filter of 560 nm (bandwidth 40 nm), an emission barrier filter of 610 nm, and an exposure time of 30 seconds.
Figure 10D:
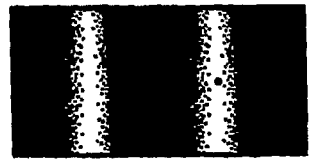
Figure 10D:
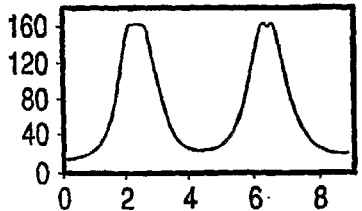

The second thermo-biolithographic step of Example 5 was performed by coating gelatin over the chitosan sub-layer (including the region previously-patterned with GFP) and using a single blade to expose the chitosan sub-layer in a band perpendicular to the GFP bands. The chip was then reacted with 1 µg/ml of NHS-rhodamine, rinsed extensively with PBS buffer and then observed with the fluorescence microscope using two filters. FIG. 10C shows a photomicrograph of the rhodamine band while FIG. 10D shows a photomicrograph and the fluorescence intensity profile of the GFP bands. The comparison of FIGS. 10B and 10D indicates that there are no obvious differences in the GFP fluorescence images or intensity profiles before and after this second thermo-biolithographic step. Thus, the casting and subsequent removal of the gelatin thermoresist does not affect the fluorescence (and presumably structure) of previously patterned GFP macromolecules.

The foregoing detailed description of the preferred embodiments of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the appended claims.

What is claimed is:

1. A method for selective deposition of molecules, comprising the steps of:
   (a) providing a reactive layer comprising a surface region coated with a resist that is biologically compatible with the reactive layer;
   (b) selectively removing a portion of the biologically compatible resist from the surface region to expose an exposed portion of the reactive layer; and
   (c) conjugating molecules with the exposed portion of the reactive layer; wherein the reactive layer comprises chitosan.

2. The method of claim 1, wherein the reactive layer comprises a polysaccharide mass.

3. The method of claim 2, further comprising depositing a selectively insolubilizable polysaccharide on a substrate to form the polysaccharide mass.

4. The method of claim 3, wherein said depositing comprises providing an aqueous solution comprising the selectively insolubilizable polysaccharide and having an initial pH, contacting the aqueous solution with the substrate, and altering the pH of the aqueous solution to insolubilize and deposit the selectively insolubilized polysaccharide on the substrate as a film of the polysaccharide mass.

5. The method of claim 3, wherein said depositing comprises providing an aqueous solution comprising the selectively insolubilizable polysaccharide and having an initial pH, electrochemically depositing the selectively insolubilizable polysaccharide on an electrically conductive support of the substrate, and altering the pH of the aqueous solution to stabilize the selectively insolubilized polysaccharide on the electrically conductive support.

6. The method of claim 1, wherein the biologically compatible resist comprises a gelatin thermoresist.

7. The method of claim 1, wherein said selective removing comprises biolithography.

8. The method of claim 1, wherein the biologically compatible resist comprises a thermoresist, and wherein said selective removing comprises melting a portion of the thermoresist and removing the melted portion of the thermoresist from the reactive layer.

9. The method of claim 8, where said melting is performed with a heated stamp applied to an exposed face of the thermoresist.

10. The method of claim 8, wherein said melting is performed with heating means incorporated in the solid support beneath the thermoresist.

11. The method of claim 1, wherein said selective removing comprises enzymatically removing a portion of the biologically compatible resist.

12. The method of claim 1, further comprising modifying the reactive layer to improve conjugatability with reactive groups of the molecules.

13. The method of claim 1, further comprising modifying the molecules to improve conjugatability with reactive groups of the reactive layer.

14. The method of claim 1, wherein the molecules comprise biomolecules.

15. The method of claim 14, wherein the molecules comprise one, two, three or more protein species.

16. The method of claim 14, wherein the molecules comprise one, two, three or more enzyme species.

17. A method for selective deposition of molecules, comprising the steps of: (a) providing a reactive layer comprising a surface region coated with a resist that is biologically compatible with the reactive layer; (b) selectively removing a portion of the biologically compatible resist from the surface region to expose an exposed portion of the reactive layer; and (c) conjugating molecules with the exposed portion of the reactive layer; wherein the molecules comprise one, two, three or more antibody species.

18. A method for selective deposition of molecules, comprising the steps of: (a) providing a reactive layer comprising a surface region coated with a resist that is biologically compatible with the reactive layer; (b) selectively removing a portion of the biologically compatible resist from the surface region to expose an exposed portion of the reactive layer; and (c) conjugating molecules with the exposed portion of the reactive layer; wherein the molecules comprise one, two, three or more receptor molecule species.

19. The method of claim 1, wherein the molecules comprise one, two, three or more nucleic acid molecule species.

20. The method of claim 1, wherein the exposed portion and the molecules comprise a first exposed portion and a first molecular species, respectively, and wherein the method further comprises the steps of:
   (d) coating the biologically compatible resist on the first molecular species conjugated to the first exposed portion of the reactive layer;
   (e) selectively removing a second portion of the biologically compatible resist to expose a second exposed portion of the reactive layer; and
   (f) conjugating a second molecular species with the second exposed portion of the reactive layer.

21. The method of claim 20, wherein the first and second molecular species are conjugated with the reactive layer sequentially.

22. A method for selective deposition of molecules, comprising the steps of: (a) providing a reactive layer comprising a surface region coated with a resist that is biologically compatible with the reactive layer; (b) selectively removing a portion of the biologically compatible resist from the surface region to expose an exposed portion of the reactive layer; and (c) conjugating molecules with the exposed portion of the reactive layer; wherein the reactive layer comprises chitosan and wherein the molecules comprise one, two, three or more antibody species.

23. A method for selective deposition of molecules, comprising the steps of: (a) providing a reactive layer comprising a surface region coated with a resist that is biologically compatible with the reactive layer; (b) selectively removing a portion of the biologically compatible resist from the surface region to expose an exposed portion of the reactive layer; and (c) conjugating molecules with the exposed portion of the reactive layer; wherein the reactive layer comprises chitosan and wherein the molecules comprise one, two, three or more receptor molecule species.

* * * * *